United States Patent
Zanin et al.

(10) Patent No.: US 10,549,025 B2
(45) Date of Patent: Feb. 4, 2020

(54) MEDICAL DEVICE IN PARTICULAR FOR THE SEPARATION OF A FLUID

(71) Applicant: ELTEK S.p.A., Casale Monferrato (Alessandria) (IT)

(72) Inventors: Massimo Zanin, Casale Monferrato (IT); Marco Pizzi, Casale Monferrato (IT); Laura Mazzucco, Casale Monferrato (IT); Marco Bertoni, Casale Monferrato (IT)

(73) Assignee: ELETEK S.P.A., Casale Monferrato (Alessandria) (IT)

( * ) Notice: Subject to any disclaimer, the term of this patent is extended or adjusted under 35 U.S.C. 154(b) by 564 days.

(21) Appl. No.: 15/036,640

(22) PCT Filed: Nov. 13, 2014

(86) PCT No.: PCT/IB2014/066015
§ 371 (c)(1),
(2) Date: May 13, 2016

(87) PCT Pub. No.: WO2015/071852
PCT Pub. Date: May 21, 2015

(65) Prior Publication Data
US 2016/0279320 A1    Sep. 29, 2016

(30) Foreign Application Priority Data
Nov. 14, 2013 (IT) .............................. TO2013A0925

(51) Int. Cl.
*A61M 1/36* (2006.01)
*A61M 1/02* (2006.01)
(Continued)

(52) U.S. Cl.
CPC ..... *A61M 1/3693* (2013.01); *A61B 5/150755* (2013.01); *A61M 1/0009* (2013.01);
(Continued)

(58) Field of Classification Search
CPC .............. A61M 1/0209; A61M 1/0213; A61M 1/0218; A61M 1/0222; A61M 1/0236;
(Continued)

(56) References Cited

U.S. PATENT DOCUMENTS 4,900,322 A * 2/1990 Adams ................ A61M 1/0209
                                                    604/248
5,269,946 A * 12/1993 Goldhaber .......... A61M 1/0222
                                                    210/257.1
(Continued)

FOREIGN PATENT DOCUMENTS

EP          1930033 A2    6/2008
WO      2010/138895 A2   12/2010
WO    WO-2011095964 A1 *  8/2011   .......... A61M 1/0209

OTHER PUBLICATIONS

Partial International Search Report for International Application No. PCT/IB2014/066015, dated Mar. 21, 2016.

*Primary Examiner* — David C Mellon
(74) *Attorney, Agent, or Firm* — Heslin Rothenberg Farley & Mesiti P.C.; Victor A. Cardona, Esq.

(57) ABSTRACT

A medical device for separating a fluid, in particular for separating platelet-rich plasma from whole blood, includes three containers and at least one corresponding connection line having an intermediate bifurcation. Provided on the connection line are valve means for enabling or preventing a flow of fluid. At least one container includes a hollow container body and a plunger associated in a movable way to the container body. A modular structure has modules connected to enable separation thereof. A first module includes at least the first container and a corresponding portion of the first connection line, and a second module, which has at least one between the second and third containers with a corresponding portion of the first connection line. Provided at least at the interface between two modules of the modular structure are releasable connectors, in particular hydraulic connectors having at least two parts that can be coupled together, each of which belongs to a corresponding module.

19 Claims, 15 Drawing Sheets

(51) Int. Cl.
*A61M 1/00* (2006.01)
*A61B 5/15* (2006.01)
*B01D 21/26* (2006.01)

(52) U.S. Cl.
CPC ......... *A61M 1/0272* (2013.01); *B01D 21/262* (2013.01); *A61M 1/0218* (2014.02); *A61M 1/0236* (2014.02); *A61M 2202/0427* (2013.01)

(58) Field of Classification Search
CPC .............. A61M 5/1413; A61M 1/3693; A61M 1/0272; A61M 1/0009; A61M 2202/0427; B01D 21/262; A61B 5/150755
See application file for complete search history.

(56) References Cited

U.S. PATENT DOCUMENTS

| | | | |
|---|---|---|---|
| 5,318,782 A | | 6/1994 | Weis-Fogh |
| 5,721,024 A | * | 2/1998 | Carmen .................... A61J 1/10 |
| | | | 422/40 |
| 7,829,022 B1 | * | 11/2010 | Lich ........................ B01L 3/502 |
| | | | 210/645 |
| 2005/0084838 A1 | * | 4/2005 | Lampeter ................ A01N 1/02 |
| | | | 435/1.3 |

* cited by examiner

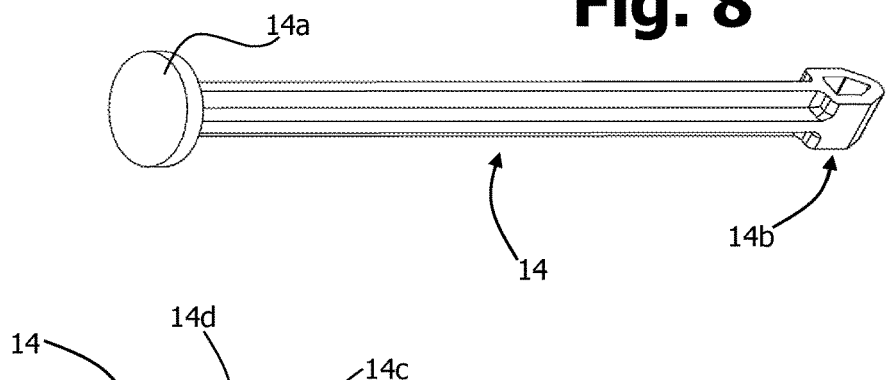
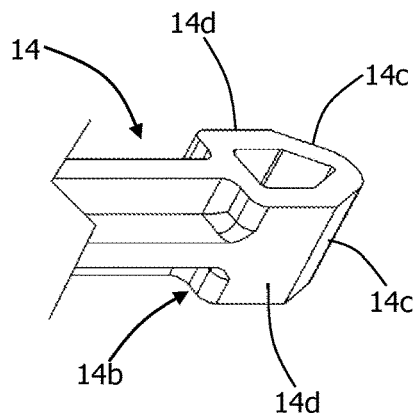
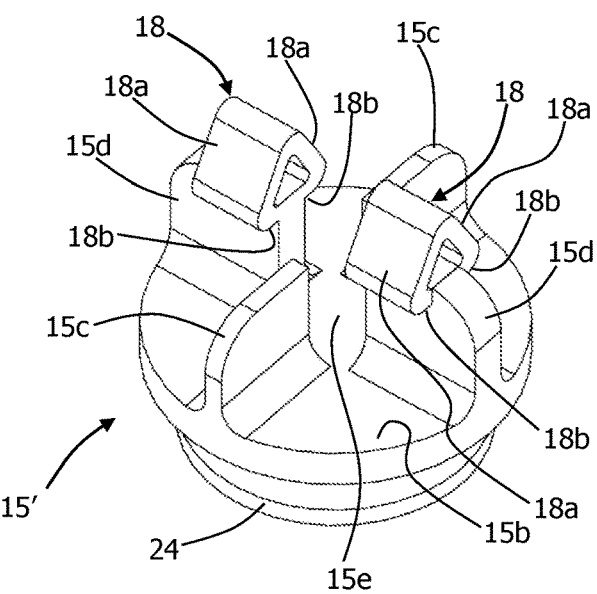
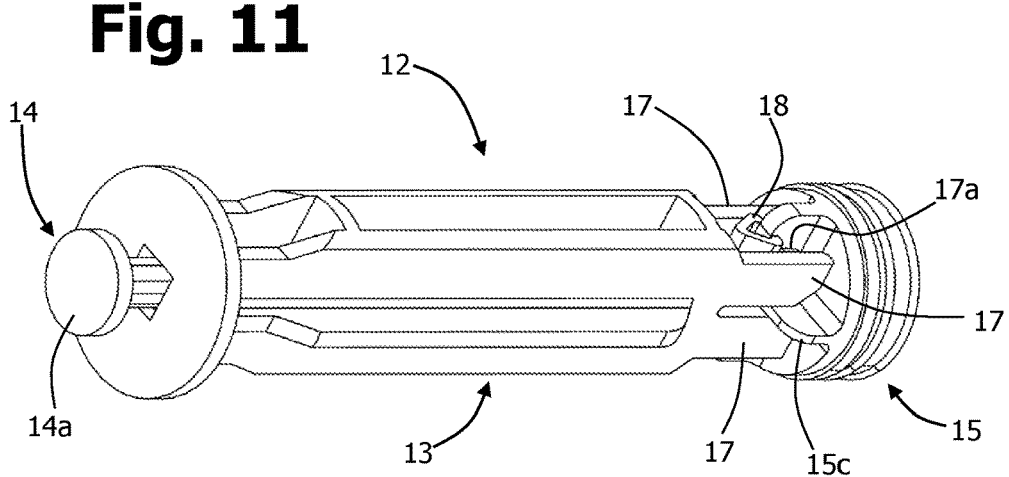

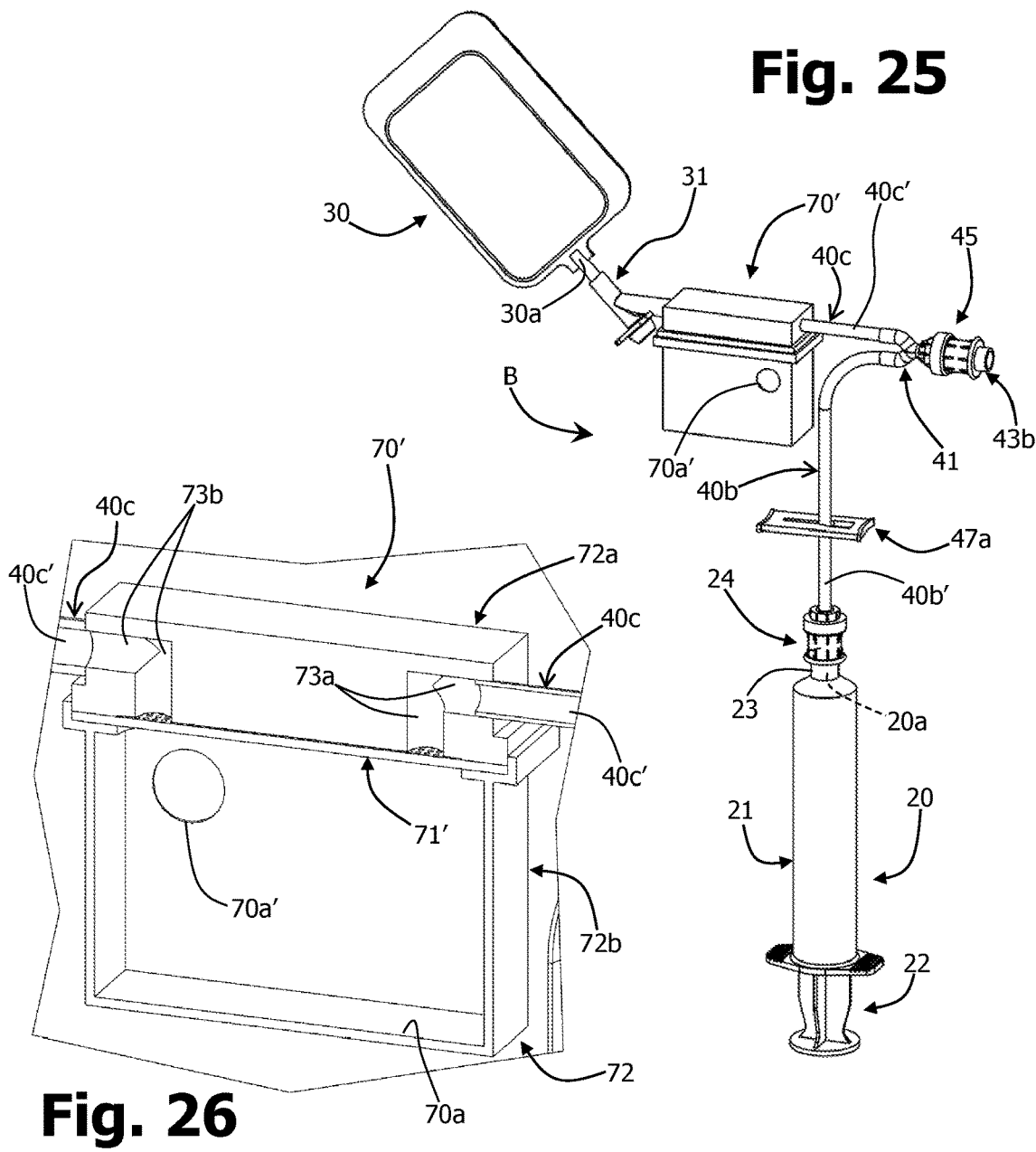
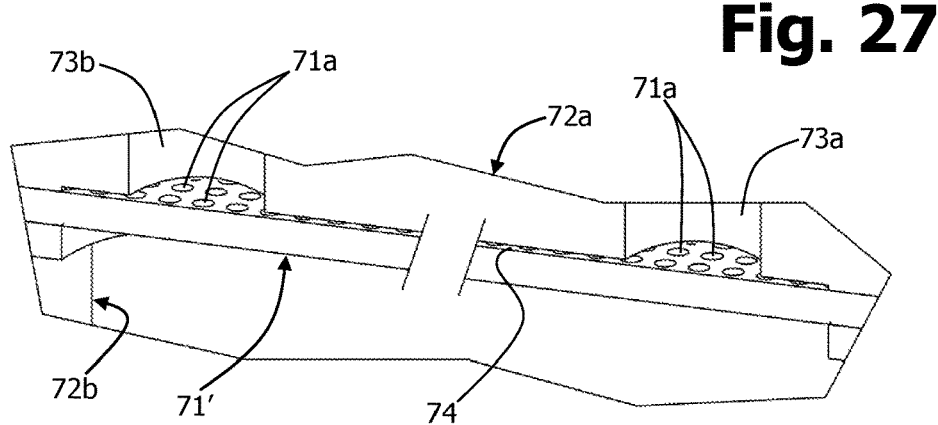

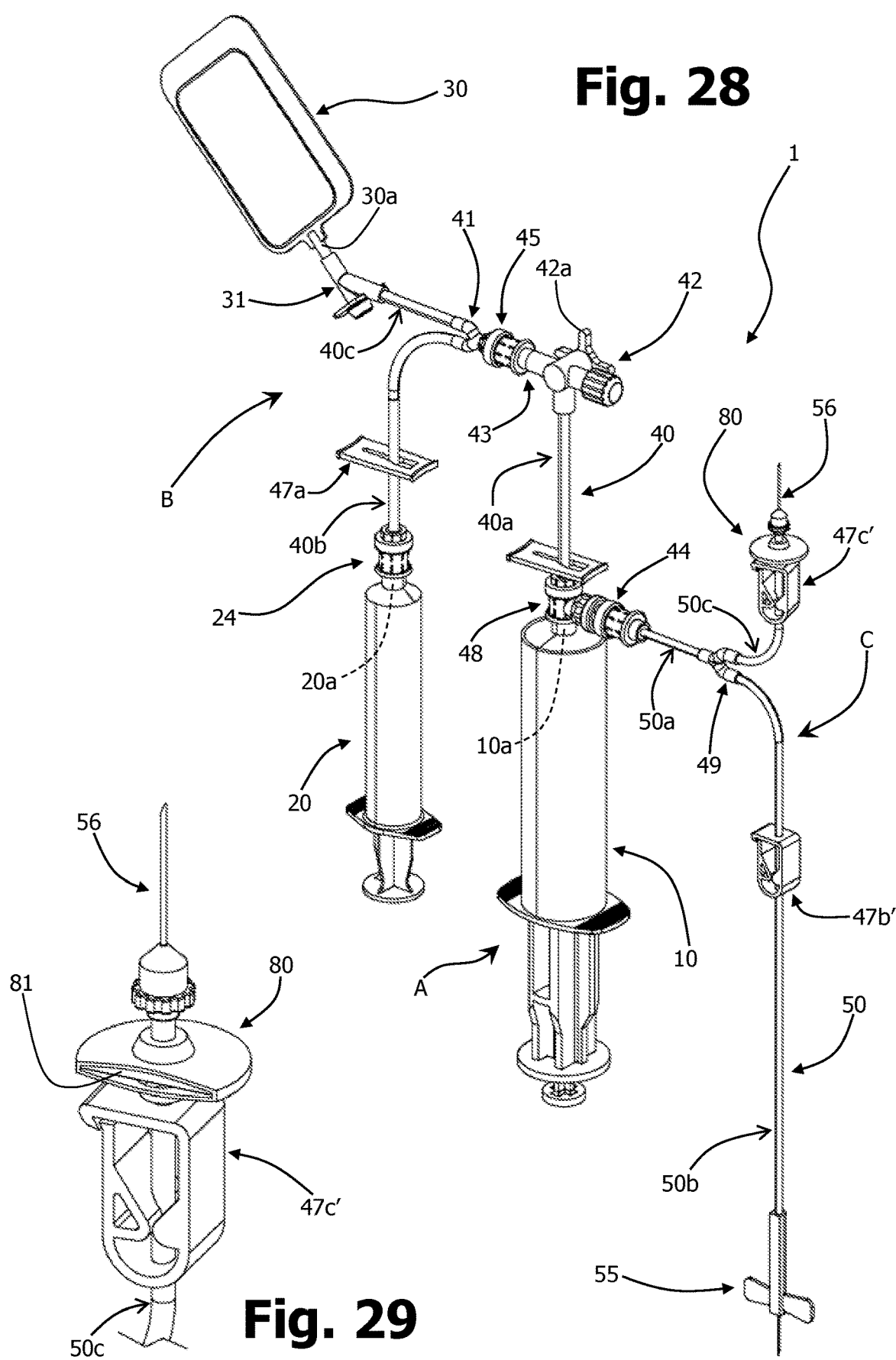

MEDICAL DEVICE IN PARTICULAR FOR THE SEPARATION OF A FLUID

CROSS REFERENCE TO RELATED APPLICATIONS

This application is a national stage filing under section 371 of International Application No. PCT/IB2014/066015, filed on Nov. 13, 2014, and published in English on May 21, 2015, as WO 2015/071852 A2, and claims priority of Italian application No. TO2013A000925 filed on Nov. 14, 2013, the entire disclosure of these applications being hereby incorporated herein by reference.

FIELD OF THE INVENTION

The present invention relates in general to medical devices, in particular medical devices for the treatment and/or control of fluids, such as biological liquids and tissues in the fluid state. The invention has been developed with particular reference to the devices that can be used for sampling a fluid from a subject, separating it into fractions and possibly obtaining a concentrate from one of the separate fractions. In this perspective, the invention has a preferred application in treatments aimed at separating platelet-rich plasma (PRP) from whole blood.

PRIOR ART

Devices of the type referred to are known and usually comprise at least three containers, constituted by pliable bag containers. In general, the blood of a patient is delivered to a collection bag, integrally connected in series to which are two transfer bags. After obstructing with a clamp the connection tube between the collection bag and the first transfer bag, the device is set in a centrifuge in order to subject the blood contained in the collection bag to soft spinning. In this way, the blood basically separates into a layer of sediment on the bottom of the collection bag, containing red and white blood cells, and a supernatant layer, containing plasma with platelets, closer to the upper part of the bag, which is provided with an outlet port. Next, the clamp is released and the collection bag is compressed in an extractor device, for forcing the plasma containing the platelets into the first transfer bag so that a fraction of the blood containing prevalently the red and white blood cells will remain in the collection bag. After obstructing once again the connection tube of the collection bag and possibly obstructing with a clamp the connection tube between the first and second transfer bags, the device is once again set in a centrifuge in order to subject the plasma with platelets to heavy spinning and thereby obtain a concentrate of platelets on the bottom of the first transfer bag and leave thereon a supernatant layer of platelet-poor plasma. With the connection tube between the two transfer bags free, the first transfer bag is compressed in order to transfer part of the layer of platelet-poor plasma to the second transfer bag, so that there will remain in the first transfer bag part of the plasma with the concentrate of platelets, which can be put back in suspension with a view to its subsequent use. The use of pliable bag containers integrally connected complicates handling of the device and renders difficult separation of the fractions of the blood in a precise way, above all when relatively small amounts of blood, in the region of 20-100 ml of whole blood, are to be treated.

There have also been proposed devices in which the container for collecting the blood to be separated is constituted by a rigid container of a syringe type, which possibly includes just one pliable transfer bag. Also these devices are, however, complicated to produce and inconvenient to use.

SUMMARY AND OBJECT OF THE INVENTION

In view of what has been set forth above, the object of the present invention is basically to provide a device of the type referred to that is simple and economically advantageous to produce, as well as being reliable, safe, precise, and convenient in operation for the operators who have to use them.

The above and other objects still, which will emerge more clearly hereinafter, are achieved according to the present invention by medical devices and methods for separating fluids, such as biological liquids and tissues in the fluid state, which present at least the characteristics referred to in the annexed claims.

BRIEF DESCRIPTION OF THE DRAWINGS

Further objects, characteristics, and advantages of the invention will emerge from the ensuing description, with reference to the annexed drawings, which are provided purely by way of non-limiting example and in which:

FIGS. 8 and 9 are a schematic perspective view of a component of the container of FIG. 5, and a corresponding detail, respectively;

FIG. 10 is a schematic perspective view of a part of a head of the plunger of FIG. 6;

FIG. 11 is a view similar to that of FIG. 6, with the component of FIG. 8 associated to the plunger, in a first condition;

FIGS. 25, 26, and 27 are views similar to those of FIGS. 22-24, regarding a module of a medical device according to a further variant embodiment of the invention.

FIG. 28 is a view similar to that of FIG. 1, regarding a further variant of the invention; and FIG. 29 is a detail, with a component partially sectioned, of a device according to the variant of FIG. 28.

DESCRIPTION OF PREFERRED EMBODIMENTS OF THE INVENTION

Figure 1:
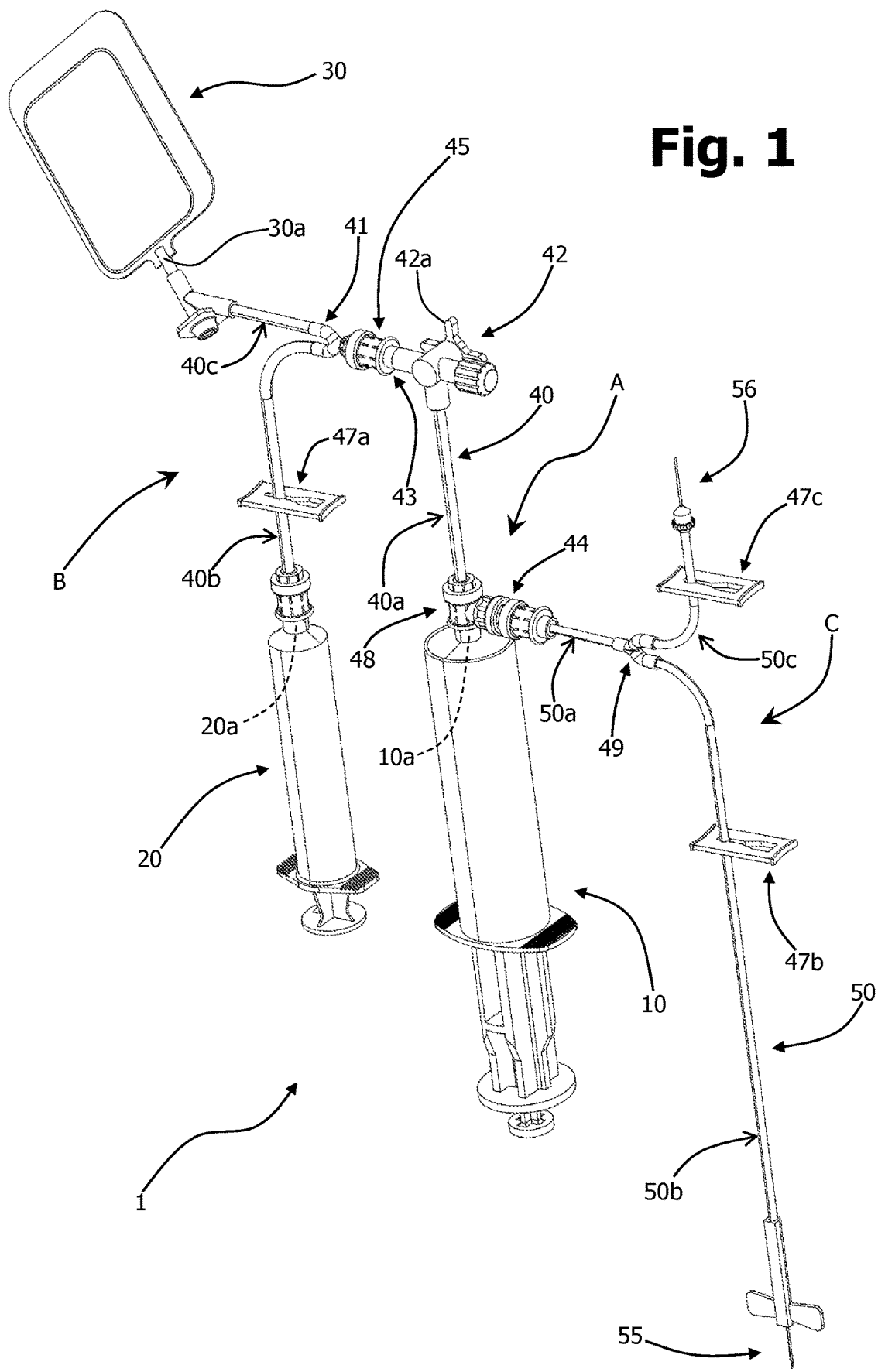
FIG. 1 is a schematic perspective view of a medical device according to one embodiment of the invention.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" and the like that may be present in various points of this description do not necessarily refer to one and the same embodiment. Furthermore, particular conformations, structures, or characteristics defined in the framework of the present description may be combined in any adequate way in one or more embodiments, which may also differ from the ones represented. Numerical references and spatial references (such as "top", "bottom", "upper", "lower", etc.) used herein are only provided for convenience and hence do not define the sphere of protection or the scope of the embodiments. Furthermore, in the present description and in the attached claims, the term "treatment", when it refers to a fluid, is to be understood in its broadest sense, and as used herein is intended to comprise activities, such as sampling of a biological or medical fluid, as well as processing thereof, for example for separating it into its fractions and/or concentrating a separated fraction thereof.

The term "fluid" is to be understood in its broadest sense, and as used herein is intended to comprise biological or medical fluids or liquids, in particular fluids or liquids comprising particles that may be at least in part separated and/or concentrated, such as cells or platelets or fragments of cells, preferably particles which contain growth factors, cytokines, and bioactive molecules. Preferably, the fluid is blood and/or its components, i.e., a biological fluid basically made up of a corpuscular part typically comprising red blood cells, white blood cells, and platelets, and a fluid part constituted by plasma.

In the figures the same reference numbers are used to designate elements that are similar or technically equivalent to one another.

In its more general terms, a medical device according to the invention, or a corresponding module, comprises at least one from among the following:

- at least one container provided with a plunger with removable stem;
- at least two containers provided with a corresponding plunger, each belonging to a corresponding module;
- at least one bag container;
- at least one needle for sampling a fluid, preferably a pair of needles;
- at least one connection line, in particular one including a tube;
- at least one hydraulic-connection attachment or connector;
- at least one self-operating valve;
- at least one valve designed to prevent any contamination of the fluid from outside following upon separation between two modules;
- at least one releasable attachment or connector having associated thereto a self-operating valve;
- at least one from among a deviator valve, a shutoff valve, and a tap;
- at least one filter, such as a separation filter and/or an anti-bacterial filter and/or a leukocyte filter;
- at least one tangential-filtration filter, in particular for concentrating a platelet-rich plasma, and/or a filter designed to provide a protection, such as an anti-bacterial filter;
- at least one identification element and/or one memory element, preferably of a wireless or radiofrequency type; and
- a plurality of modules that can be separated during different steps of use of the device.

A possible embodiment of a medical device for separating a fluid is represented schematically by way of example in FIG. 1, the device being designated as a whole by 1. In what follows, it is to be assumed that the fluid considered is whole blood and that the device 1 is used for separation of platelet-rich plasma, for example for regenerative applications and/or for physiological renewal and/or tissue repair in specialist clinical sectors, such as orthopaedics, plastic surgery, and maxillo-facial surgery.

The device according to the invention preferentially comprises disposable components provided in sterile packaging. Very preferably, the device comprises all the components necessary for taking a blood sample from a patient, preventing coagulation of the blood, separating the sample into its fractions, and obtaining a concentrated fraction. In more general terms, the device enables treatment of a fluid in a closed system, i.e., in conditions such as to prevent any contamination of the fluid itself from outside during the various operating steps.

In the example illustrated, the device 1 comprises a container 10 for receiving the fluid to be treated, here whole blood, a container 20 for receiving a first fraction of the fluid, and a container 30 for receiving a second fraction of the fluid. As will emerge clearly hereinafter, the container 10 is a container for centrifuging the fluid, suitable for being set in a centrifuge. In a preferred, but not exclusive, embodiment, also at least one other between the container 20 and the container 30 may be a container suitable for being set in a centrifuge in order to subject a fraction of the starting fluid to centrifuging.

The three containers each have a first port for fluid inlet and/or fluid outlet, designated, respectively, by 10a, 20a and 30a, to which there can be associated the ends of a hydraulic connection line, comprising, for example, one or more transparent pliable tubes. In greater detail, the aforesaid line, designated as a whole by 40, includes a first line branch 40a, with a first inlet end that can be associated to the port 10a of the container 10 and at least one intermediate bifurcation 41, comprising, for example, a wye or tee, so as to define at least one second line branch 40b and one third line branch 40c. The branches 40b and 40 each define an outlet end of the line 40, which can be associated to the ports 20a and 30a of the containers 20 and 30, respectively. Preferentially, operative on the connection line 40 are valve means, such as shutoff valve means or flow-deviator valve means, designated as a whole by 42, which can be operated for enabling or preventing a flow of fluid through the branch 40b and/or the branch 40c.

According to a characteristic of the invention, the device 1 has a modular structure; i.e., it comprises a plurality of stages or modules that are connected together in a separable way, for enabling separation according to the operating step of use of the device 1.

Preferably, the device 1 envisages an initial configuration in which all the modules provided, for example two or three modules, are associated to one another and sterilized, in particular for defining a device in which the inside of all the components—such as containers of the fluid and/or fractions thereof, as well as corresponding connection lines and valve means—is sterile and protected from any contamination from outside, enabling maintenance of a condition of sterility of the fluid and of its separated or concentrated fractions during the various operating steps of use of the device 1.

The aforesaid modules include at least one first module, designated as a whole by A, which comprises the container 10 and a corresponding portion (40a) of the line 40, and a second module, designated as a whole by B, which comprises at least one between the container 20 and the container 30, with a corresponding portion (40b and/or 40c) of the line 40. In a preferred embodiment, such as the one represented, the module B includes both of the containers 20 and 30 with the corresponding line branches 40b and 40c, but not excluded from the scope of the invention is the case where the container 20 and the branch 40b, on one side, and the container 30 and the branch 40c, on the other, belong to two different modules of the modular structure.

According to a further characteristic of the invention, provided at least at the interface between two modules of the modular structure of the device 1 are hydraulic connectors, in particular of the type comprising at least two parts that can be coupled together mechanically in a fluid-tight way, designed to provide both a hydraulic connection between the modules, enabling passage of the fluid, and a mechanical connection between the modules to enable easy handing of the device 1. Preferably, the connectors are of the separable or releasable type, in particular for enabling convenient separation between the modules in question.

With reference to the example represented, designated by 43 is such a releasable connector, operatively set between the modules A and B.

Preferentially, the connector 43 is provided upstream of the bifurcation 41 and downstream of the valve means 42, but in various embodiments (not illustrated) there may be provided two distinct releasable connectors set downstream of the bifurcation 41, in addition or as an alternative to the connector 43, each on a corresponding branch 40b and 40c of the line 40. As will emerge clearly hereinafter, the releasable connectors provided are preferentially formed by two parts or attachments that can be coupled together, each of which belongs to a corresponding module of the device 1, the connectors being preferably of a screw or threaded type, even though they may be of some other fast-engagement and/or fast-release type.

The container 10 is preferably a container having a rigid structure and may possibly be used for direct sampling of the fluid to be subjected to treatment and/or of a corresponding auxiliary substance: in this case, the container 10 may be a container of a syringe type, which may be equipped with a corresponding sampling needle. However, in a preferred embodiment of the invention, the device 1 comprises at least one further connection line, designated as a whole by 50, for setting in fluid communication the connection line 40, in particular its first branch 40a, with at least one between a first sampling device 55 for sampling the fluid and a second sampling device 56 for sampling an auxiliary substance of the process. In the case exemplified herein, where the device 1 is used for separating whole blood, the first sampling device 55 fluid is a needle or cannula for venous sampling, whereas the second sampling device 56 can be a needle, for sampling an anti-coagulant from a container not belonging to the device 1. In a different embodiment, the second device 56 fluid is constituted directly by a container of the auxiliary substance.

One or both of the aforesaid sampling devices 55 and 56 may possibly belong to the module A, with the corresponding connection line 50 connected to the connection line 40. However, in a particularly preferred embodiment of the invention, at least one of the sampling devices 55 and 56 belongs to a further module of the structure of the device 1 that is different from the modules A and B. In the example represented, the aforesaid further module is designated by C and comprises both of the sampling devices 55 and 56. In the embodiment exemplified, where both of the sampling devices 55 and 56 are provided, the connection line 50 includes an outlet branch 50a, for connection to the first branch 40a of the first connection line 40, as well as two inlet branches 50b and 50c, which are each connected to a respective sampling device 55, 56 and converge into the outlet branch 50a. Also, preferably provided at the interface between the modules A and C is a releasable connector 44, for example of the same type as the connector 43.

Preferentially, the device 1 comprises one or more self-operating valves, including self-closing valves, which can be at least in part integrated in a corresponding hydraulic connector for connection between two modules, or else operatively set in the proximity of the aforesaid connector.

In a preferred embodiment, for example, at least one self-operating valve 45 is provided, configured for enabling a flow from the branch 40a to the branch 40b and/or 40c and for preventing any reflux from the branch 40b and/or from the branch 40c of the line 40 to the corresponding branch 40a and/or for automatically closing the passage towards the branches 40b and/or 40c preventing any contamination from outside in the case of separation of the parts of the connector 43. As will be seen, such a valve may be integrated in a part of the connector 43, on the branch 40a upstream of the bifurcation 41 and downstream of the valve means 42. In one embodiment, such as the one exemplified, the valve means 42 belong to the module A, whereas the valve 45 belongs to the module B.

In the case where the module C is provided, or in any case at least one sampling device 55 and/or 56 is provided, a self-operating valve may be provided for enabling a flow from the line 50 to the line 40 and preventing any reflux from the line 40 to the line 50 and/or for automatically closing the passage towards the line 40 and/or container 10 preventing any contamination from outside in the case of separation of the parts of the connector 44. Preferentially, but not necessarily, the aforesaid self-operating valve—not indicated in FIG. 1 in so far as it is integrated in the attachment or connector designated by 48—is provided substantially in an interface area between the branch 40a of the line 40 and the branch 50a of the line 50. As will be seen, in one embodiment, this self-operating valve belongs to the module A.

The self-operating valve or valves envisaged by the device 1 may advantageously be configured as one-way or non-return valves, or possibly deviator valves or shutoff valves.

One or more modules of the structure of the device 1 may also comprise at least one further shutoff member on at least one branch of a corresponding connection line 40 or 50, such as, for example, one or more clamp valves, some of which are designated by 47a, 47b and 47c and hereinafter defined for simplicity as "clamps".

Figure 2:
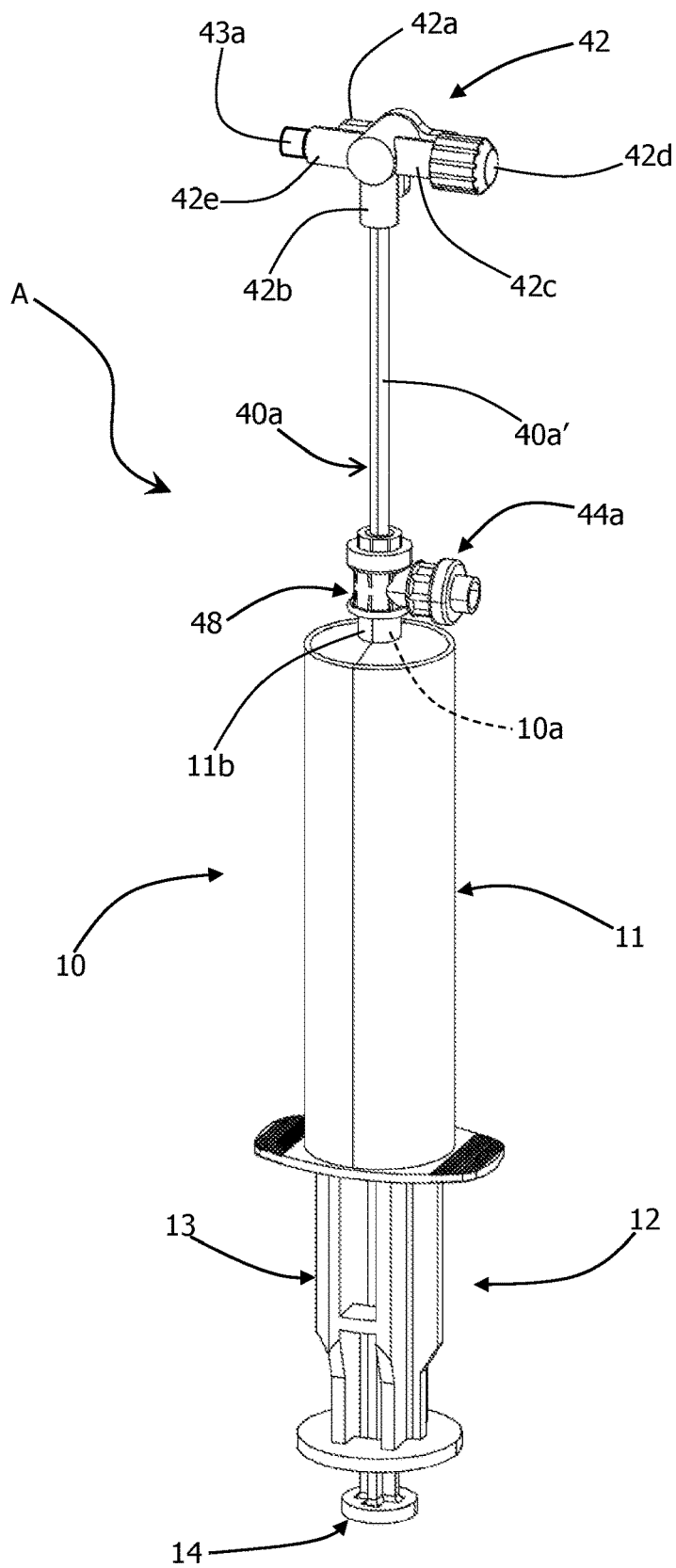
FIGS. 2 and 3 are schematic perspective views of two modules of a medical device according to one embodiment of the invention.

Represented in FIG. 2 is an embodiment of the module A, basically constituted by a disposable sterile set, comprising the container 10, preferably having a rigid structure, and a corresponding part of the connection line 40, in particular its branch 40a, and the valve means 42.

The branch 40a preferentially comprises a pliable tube 40a', for example made of PVC or other elastomer. The tube 40a' may indicatively have an internal diameter of 2.8 mm, an external diameter of 4 mm, and a length of approximately 60 mm.

The valve means 42 preferentially comprise a shutoff valve or a tap, in particular of a mechanical type, namely with a manually operated and/or mechanically operated control element, without any electrical connection. In the embodiment exemplified, the above valve is a deviator valve, here constituted by a three-way tap, with corresponding knob or control element 42a. In the example, one of the three ways is closed with a plug, and in alternative embodiments (not represented) the valve in question may be a valve or tap with just two ways (an inlet and an outlet), of an open or closed type.

One way 42b of the tap 42 is in fluid communication, via the tube 40a', with the port 10a of the container 10. For this purpose, the inlet end of the tube 40a' is provided with an attachment 48, configured for coupling with a corresponding attachment 11b of the container 10 defining the port 10a. In one embodiment, the coupling between the attachments 48 and 11b is of a fast type, preferably of a Luer type. On the other hand not excluded are other types of coupling (a screw coupling, a bayonet coupling, a snap-in coupling, etc.).

A second way 42c of the tap 42 is closed by a plug 42d, whilst the remaining way 42e of the tap includes or has associated thereto a part 43a of the hydraulic connector 43 of FIG. 1, which is preferably a threaded connector. In the example, the ways 42c and 42e of the tap 42 are provided for this purpose with a thread, preferably of a male type.

In the case where the device 1 according to the invention comprises the module C, the attachment 48 may be a three-way connector, such as a tee, in order to enable connection of the line 50, in particular of its branch 50a (FIG. 1), to the line 40, in particular to its branch 40a. In the example represented, the attachment 48 also defines a part 44a of the hydraulic connector 44 of FIG. 1, which is also preferentially a threaded connector, preferably of a male type. As explained hereinafter, on the other hand, in a different embodiment, the module C could be connected to the way 42c of the tap 42.

As has been said, in one embodiment, at least one self-operating valve of the device 1 is integrated at least in part in a hydraulic connector or attachment. Preferably, such a self-operating valve comprises an open/close element and a resilient element, such as a spring, preferably a helical spring. The resilient element that determines automatic closing of the open/close element preferably has a pre-defined or calibrated force, for example to prevent movement of the open/close element in the presence of values of pressure different from the predefined ones (such as a valve that does not open with values of negative pressure on one side of the open/close element and/or of positive pressure on the opposite side that are higher than a predefined value).

The self-operating valve, preferably a fast-operating valve, can perform the function of shutting off or automatically deviating the flows during certain steps of use of the device 1, or automatically closing a line of a part or module of the device, in particular for preventing any leakage of fluid and/or contamination from outside. The self-closing device or valve is preferably of a fast type.

For instance, in FIG. 2 a self-operating valve (described hereinafter) is integrated in the attachment 48, and specifically in its part 44a. As explained hereinafter, on the other hand, such a valve may be omitted, in configurations of the device 1 different from the one illustrated (or possibly replaced by a valve designed to close automatically upon detachment of the part 44b of the connector 44).

Figure 3:
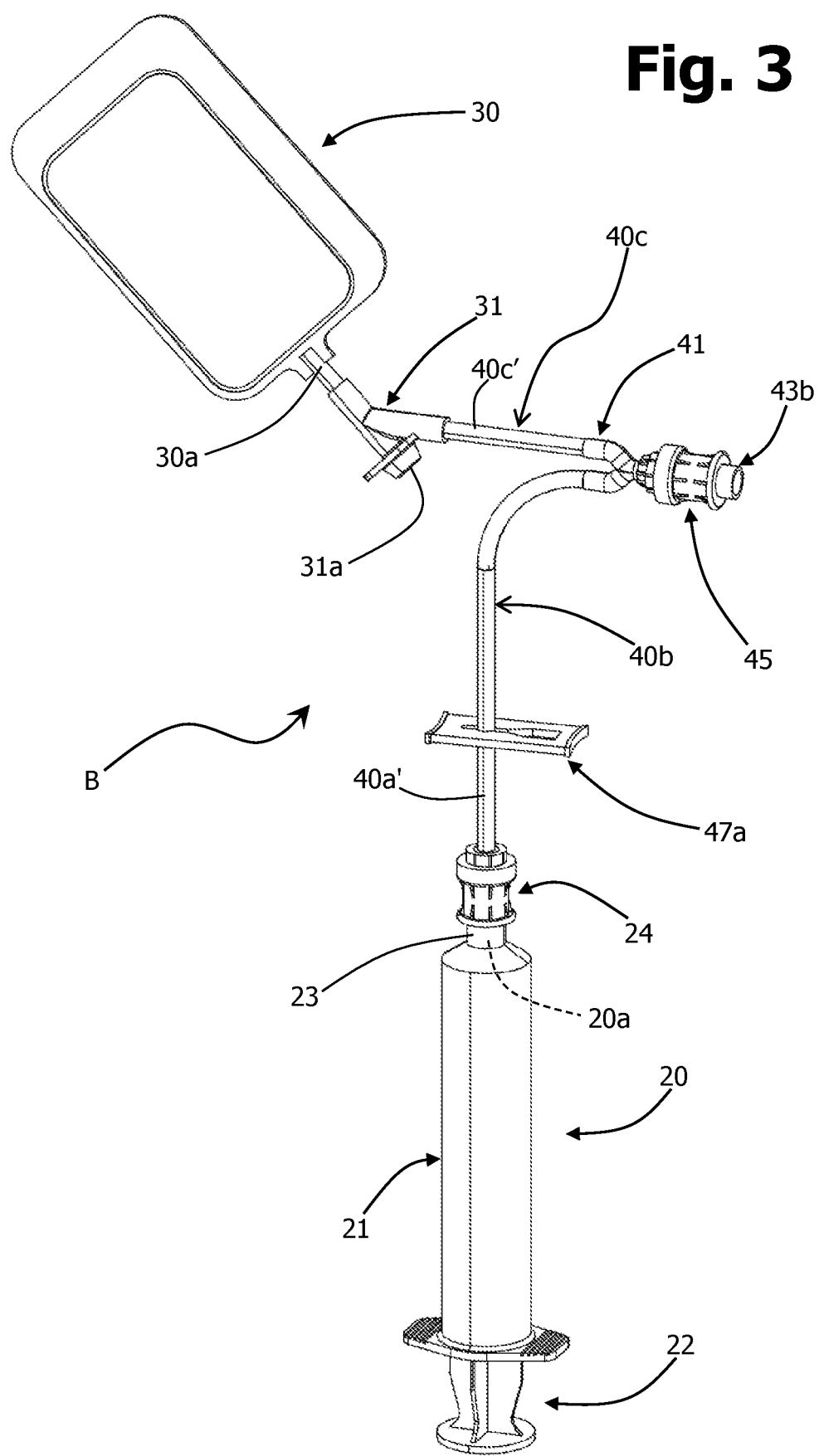

Represented in FIG. 3 is a possible embodiment of the module B, which is also basically constituted by a disposable sterile set, comprising the containers 20 and 30, the corresponding parts of the connection line 40, in particular its branches 40b, 40c with the bifurcation 41, a part 43b of the connector 43, preferably with a threaded attachment, and a self-operating valve 45. In a preferred embodiment, such as the one represented, the container 20 is a container of a syringe type, hence with a rigid structure, comprising a generally elongated container body or barrel, designated by 21, and a plunger, designated by 22, which is associated in a movable way to the barrel 21. The plunger 22 includes a plunger stem and a plunger head, here not represented but designated by 22a and 22b in FIG. 15, which are fixed with respect to one another. The container 20 may be a commonly used disposable syringe, for example with a capacity of 20 or 30 ml, but in possible variant embodiments the container 20 may be of the same type described hereinafter as the container 10, i.e., of the type in which the head and the stem of the plunger are coupled in a separable way. At its distal end the barrel 21 has an attachment 23, preferably a fast attachment, for example of a Luer type, defining the port 20a.

The container 30 is preferentially a generally pliable and/or compressible container, in particular a bag container, for example with a capacity of 30 or 60 ml, made, for example, of polymeric plastic material, such as EVA, or an elastomer. Preferentially, associated to the port 30a of the container 30 is a connector 31, for example a wye having an area 31a that can be perforated with a needle, such as a membrane made of elastomer.

The branches 40b and 40c preferentially comprise respective pliable tubes 40b' and 40c', in particular of the same type and dimensions in cross section as the tube 40a'. The tubes 40b' and 40c', which may indicatively have a length of 60 and 80 mm, respectively, each have a first end connected to a respective way of the connector defining the bifurcation 41. The second end of the tube 40b' is provided with an attachment 24, configured for coupling with the attachment 23 defining the port 20a. Preferentially, the coupling between the attachments 23 and 24 is of a Luer type, even though other types of coupling (a screw coupling, a bayonet coupling, a snap-in coupling, etc.) are not excluded. The second end of the tube 40c' is instead connected to the connector 31 associated to the port 30a of the container 30.

Associated, either directly or with interposition of a corresponding tube, to the connector defining the bifurcation 41, on the opposite side with respect to the tubes 40b' and 40b', are the connector 43 and the self-operating valve 45. Preferentially, the body of the valve 45 is shaped, on the side opposite to the bifurcation 41, for providing a respective part 43b of the hydraulic connector 43, which is to couple to the part 43a associated to or defined by the tap 42 (FIG. 2).

In one embodiment, on at least one of the branches 40b and 40c, in particular downstream of the bifurcation 41, at least one shutoff member is provided. Such a case is exemplified in FIG. 3, where designated by 47a is a clamp on the branch 40b. In a different embodiment, the clamp 47a may be on the branch 40c or on both of the branches. The presence of the clamp 47a, albeit preferable for practical reasons, is not to be understood as essential, given that it may possibly be replaced by other shutoff means or by a self-operating valve.

Figure 4:
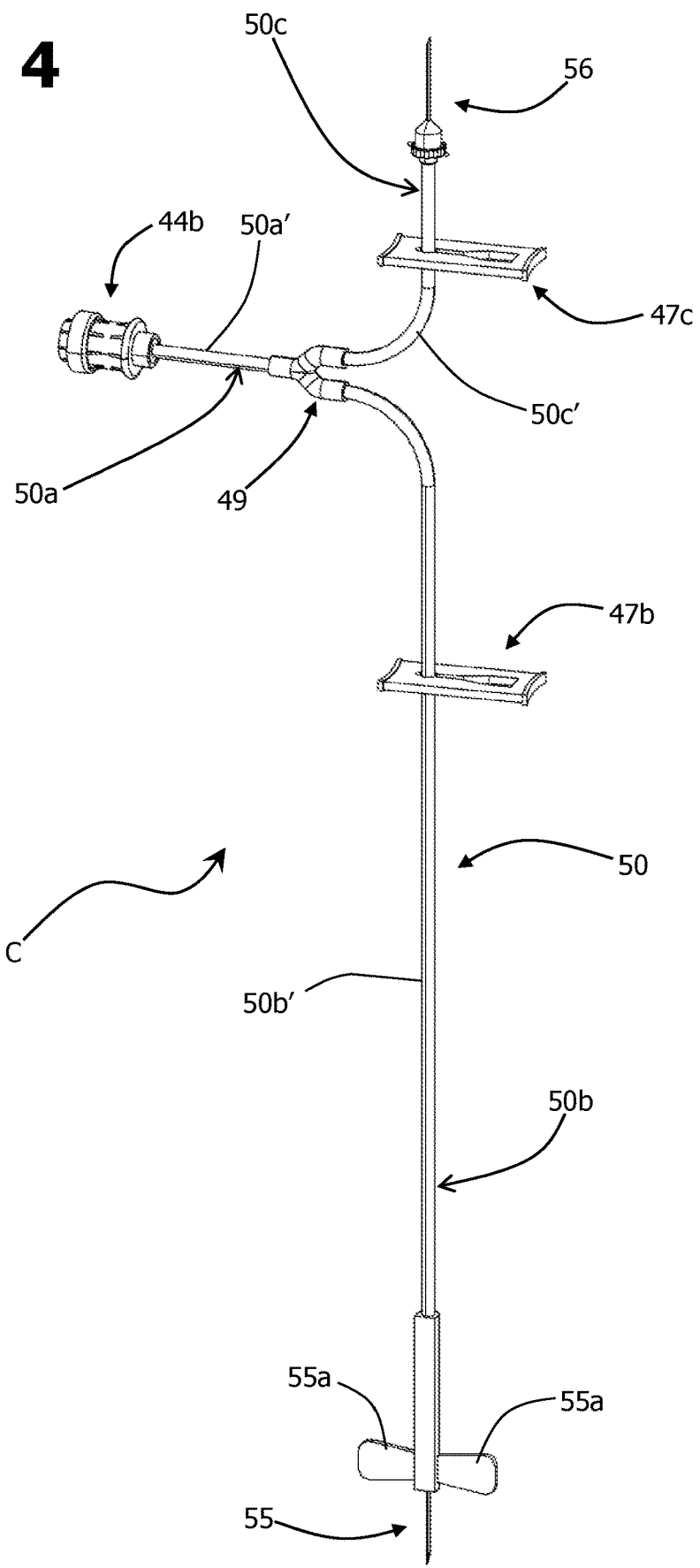
FIG. 4 is a perspective view of a further module of a medical device according to a preferred embodiment of the invention.

Represented in FIG. 4 is a possible embodiment of the module C, which is also basically constituted by a disposable sterile set. In the example, the module C comprises sampling devices 55 and 56 and the connection way 50.

The device 55 is here constituted by a needle preferably provided with tabs 55a for fastening to the patient from whom the blood sample is to be taken. Likewise, the device 56 comprises a further needle, for sampling an anti-coagulant or other auxiliary substance from a container not belonging to the device 1. In possible variants, as already mentioned, the device 56 may consist of a container for the anti-coagulant or other auxiliary substance.

The branches 50b and 50c of the connection line 50 comprise pliable tubes 50b' and 50c', preferably made of polymeric or elastomeric material, such as silicone or PVC, for example with a length of 300 and 80 mm, respectively, the ends of which opposite to the needles are connected to the inlet ways of an intermediate connector 49, in particular a three-way tee or wye. The branch 50a of the line 50 also comprises a tube 50a', preferably of the same type as the ones used for providing the line 40, for example 60 mm long. The first end of the tube 50a' is connected to the outlet way of the connector 49, whilst associated to its second end is a corresponding part 44b of the hydraulic connector 44 of FIG. 1, for coupling with the part 44a of FIG. 2. As has been said, the coupling is preferably of a threaded type.

In a preferred embodiment, provided on at least one of the branches 50b and 50c, in particular upstream of the connector 49, is a shutoff flow member: illustrated in FIG. 4 is the case where both of the branches referred to are provided with clamps similar to the clamp 47a, designated by 47b and 47c, respectively.

In one embodiment of the invention, the container 10 of FIG. 2 is shaped substantially as a syringe for injection and/or fluid sampling, and as such comprises a generally elongated container body or barrel, designated by 11, and a plunger, designated by 12, associated in a movable way to the barrel 11.

In general terms, the plunger 12 has a plunger head (not represented in FIG. 2) that is slidably engaged in a fluid-tight way within barrel 11, for defining thereby a chamber for collecting the fluid that is in communication with the port 10a. Connected to the plunger head is a plunger stem 13, which can be displaced in the barrel 11 for moving the plunger head, and thereby varying the volume of the collection chamber for introducing the fluid therein or expelling it therefrom, respectively. The stem 13 is connected in a releasable way to the plunger head via a coupling arrangement that comprises first coupling means, at a distal end of the stem, and second coupling means, on a face of the plunger head that is opposite to the first end of the container body.

The aforesaid coupling arrangement may be of any type known in the sector, for example with a bayonet coupling, a threaded coupling or, in general, an arrangement in which coupling and decoupling between the stem and the head is obtained via angular movements of the former with respect to the latter. However, in a preferred embodiment of the invention, the aforesaid arrangement is obtained according to the Italian patent application entitled "Medical device for the treatment of fluids", filed on the same date by the present applicant, the teachings of which are incorporated herein for reference. In brief, according to the solution proposed by the present applicant, the container 10 comprises a maneuvering shaft 14, which is slidably mounted on the plunger stem 13 and can be operated manually for causing disengagement between the aforesaid first and second coupling means, and if need be facilitating their mutual engagement.

Preferentially, the aforesaid coupling means may be engaged to one another and disengaged from one another in a way at least in part elastic. Once again preferably, the stem 13 and the shaft 14 are substantially coaxial.

A possible embodiment of the container 10, which may, for example, have a capacity of 60 ml, is illustrated in FIGS. 5-14.

Figure 5:
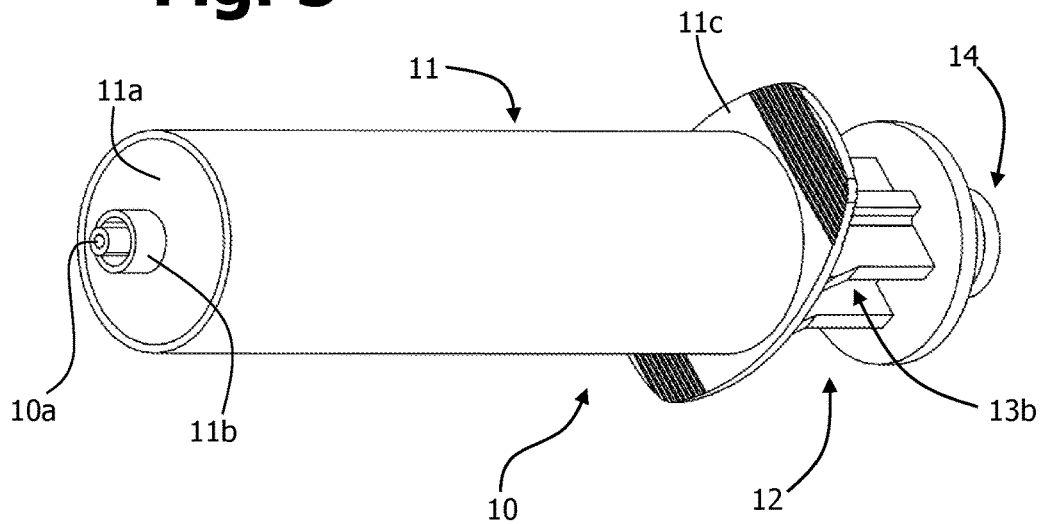
FIG. 5 is a schematic perspective view of a first container of a syringe type of a medical device according to one embodiment of the invention.
Figure 6:
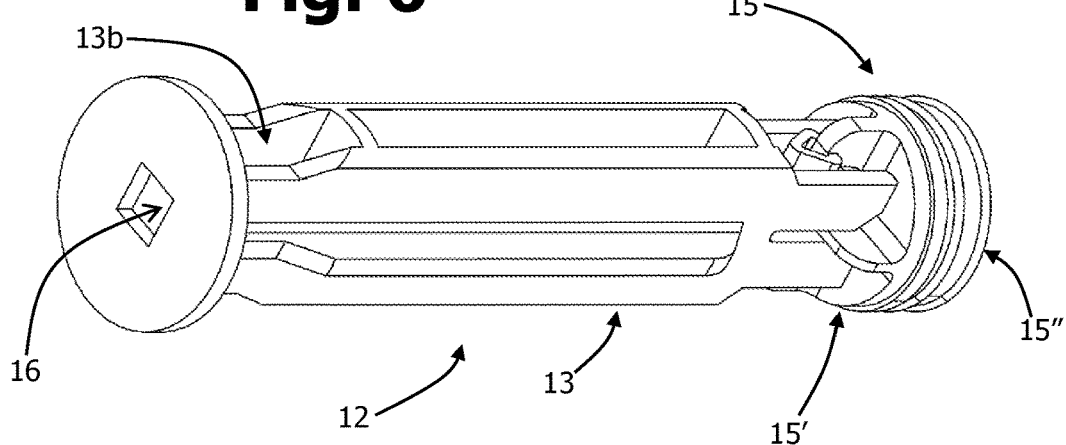
FIG. 6 is a schematic perspective view of a plunger of the container of FIG. 5.

With reference to FIG. 5, the barrel 11 has an end wall 11a provided with the attachment 11b. The opposite end of the barrel 11 has a second port (not represented) for insertion and sliding of the plunger 12. In one embodiment, substantially at the aforesaid second port, the barrel 11 has a flange 11c projecting outwards for facilitating manual gripping of the container 10 and/or its anchorage to an automated-treatment apparatus (here not represented). With reference to FIG. 6, the plunger 12 comprises, at its distal end, a plunger head 15 for slidable engagement in a fluid-tight way in the barrel 11, for defining therewith a chamber for collecting the fluid, which is in communication with the port 10a. The plunger 12 includes the plunger stem 13, which is connected to the head 15 and can be displaced for moving the head itself and thereby varying the volume of the aforesaid collection chamber, in order to admit or expel the fluid, respectively, as in a syringe. In one embodiment, the plunger head 15 comprises a cap or core 15' made of relatively rigid material and a coating part made of generally elastic material, which forms a gasket 15", designed to guarantee the necessary seal of the head 15 with respect to the inner surface of the barrel.

In the preferred embodiment, the stem 13 is connected in a releasable way to the head 15, via a coupling arrangement that comprises first coupling means, at a distal end of the stem 13, and second coupling means, on a face of the head 15 that is opposite to the port 10a. The stem 13 is shaped so as to define a seat 16, within which the shaft 14 is axially slidable from an inoperative position to an operative position, for causing disengagement between the aforesaid first and second coupling means. If need be, the shaft 14 may also be made to slide from the inoperative position to the operative position, in order to cause or facilitate mutual engagement between the aforesaid coupling means.

Figure 7:
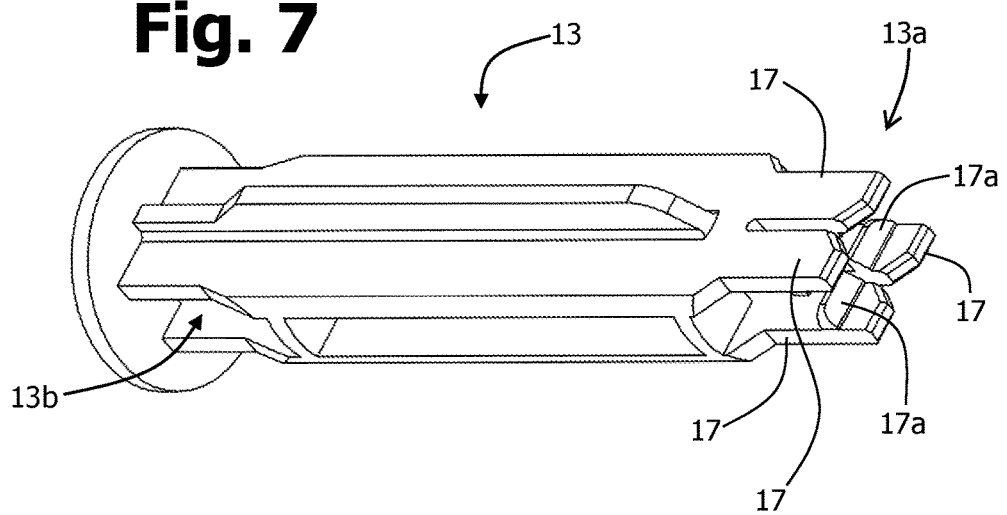
FIG. 7 is a schematic perspective view of a stem of the plunger of FIG. 6.

Visible in FIG. 7 is the distal end of the stem 13, here designated as a whole by 13a. In one embodiment, the aforesaid first coupling means include a plurality of elastically deformable coupling or engagement elements, in particular at least two coupling elements, preferably opposed to one another, it being, however, possible for a single coupling element to be provided. With reference to the example illustrated, these coupling elements basically comprise two opposed pairs of tabs 17, at the distal end 13a of the stem 13. According to embodiments (not represented), at the bottom end of the stem 13 just two opposed tabs 17 could be provided or, in the limit, even just one elastically deformable tab 17, on just one side of the stem. In the example, each tab 17 has, on its innerside, an engagement relief or tooth 17a, which preferentially extends in a transverse direction over the tab.

The maneuvering shaft 14 (visible in FIGS. 8-9) has a control portion 14a and an actuation portion 14b shaped for interacting with the tab or tabs 17. For this purpose, in one embodiment, the portion 14b comprises at least one inclined plane, configured for interacting with at least one surface of a corresponding tab 17 of the stem 13, in particular a relief thereof 17a. With reference to the example represented, as may be clearly seen in FIG. 9, the end surface of the portion 14b is distinguished by the presence of two inclined planes 14c that are opposed and divergent towards the end 14a of the shaft 14, each of these inclined planes being radiused to a generally plane surface 14d. In the example, the surfaces 14d are substantially parallel.

The second coupling means provided on the plunger head 15 comprise at least one second coupling element, with respect to which an aforesaid first coupling element (here represented by a tab 17 of the stem 13) can be engaged/disengaged. Visible in FIG. 10 is a possible embodiment of the plunger head, and in particular of its core 15', which preferably has a generally circular shape. In the example, the core has a substantially disk-shaped main wall 15b, from the upper face of which there rise two pairs of radial walls 15c and 15d, which define a central space 15e between them. Provided at the upper end of at least one wall 15d is at least one respective second coupling or engagement element 18. The element 18 preferentially comprises, at least one part—such as a step or an engagement element and/or an inclined plane—configured for interacting with a surface of a corresponding first coupling element (i.e., a tab 17, in the example). In the example of FIG. 10 two elements 18 are provided, the upper ends of which are distinguished by the presence of two inclined planes 18a opposed and divergent towards the wall 15b, each of which is radiused to a surface that is generally transverse or perpendicular to the wall 15d so as to define a respective step or engagement 18b.

Figure 12:
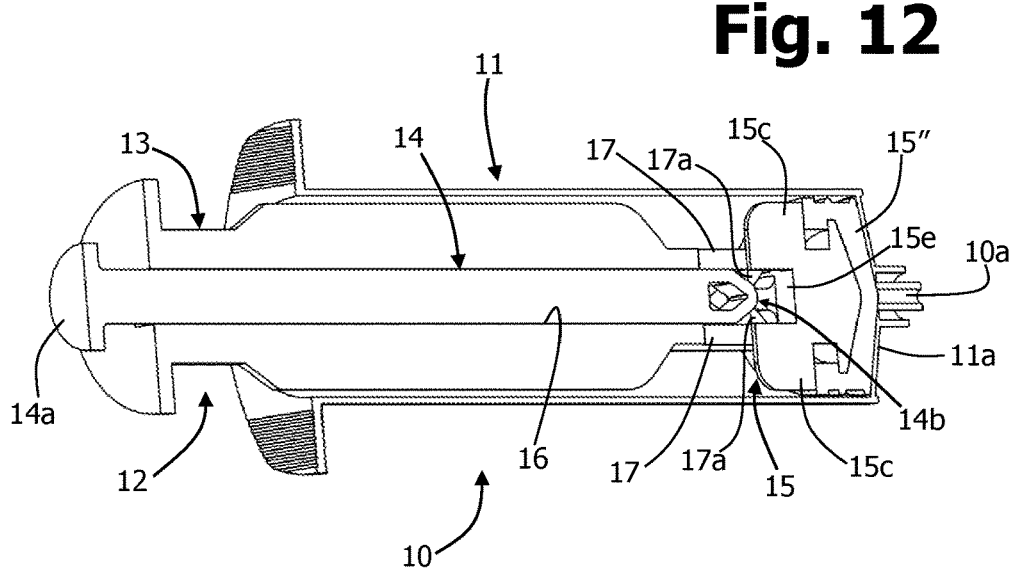
FIG. 12 is a schematic cross section of the container of FIG. 5, in the condition of FIG. 11.

FIGS. 11-12 illustrate the condition where the head 15 is coupled to the stem 13 of the plunger 12. It should be noted that, merely for a more convenient understanding, in FIG. 12, the head 15 is represented in the position of maximum advance. In this condition, the reliefs 17a of the tabs 17 (for their part external to the space 15e of FIG. 10) engage with the steps 18b of the coupling elements 18, with the tabs 17 substantially straight or in a predefined position, i.e., substantially not subjected to elastic stress. In the coupled condition, with or without the maneuvering shaft 14, the container 10 can be used as a syringe, for the purposes of sampling a fluid through the port 10a defined by the attachment 11b.

Figure 13:
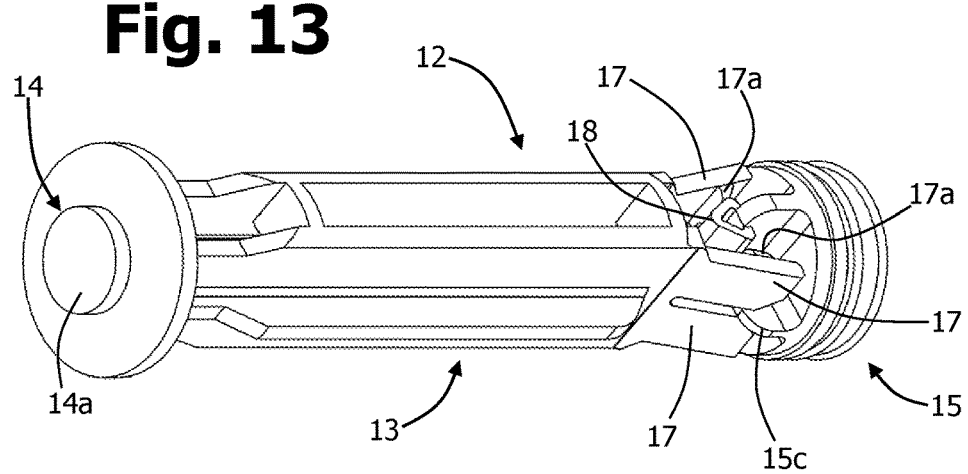
FIGS. 13 and 14 are views similar to those of FIGS. 11-12, in a second condition.
Figure 14:
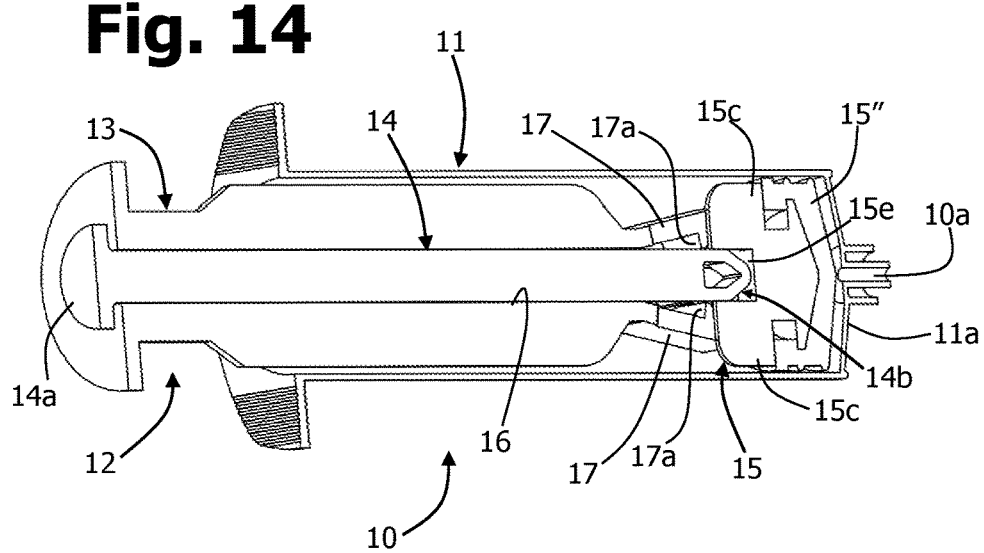

In the case where it becomes necessary to separate the stem 13 from the head 15, for example for putting just the barrel 11 in a centrifuge, the shaft 14 is to be pushed towards the inoperative position of FIGS. 13-14 (which are similar to FIGS. 11-12, but represent a condition of decoupling between the stem and the head). The thrust exerted on the shaft 14, while the stem 13 is withheld, causes application of a force on the tabs 17, and in particular on the part of their teeth or reliefs 17a. The "wedge-shaped" portion defined by the inclined planes 14c (FIG. 9) of the actuation portion 14b of the shaft 14 penetrates progressively between the reliefs 17a of the pairs of opposed tabs 17 (for their part facing the space 15e), causing elastic divarication of the tabs themselves, as may be seen in FIGS. 13-14. After extraction of the stem 13 with the shaft 14, the barrel 11 can be processed as required, for example by putting it into a centrifuge (after obstructing the port defined by the attachment 11b or the tube associated to the attachment).

Figure 15:
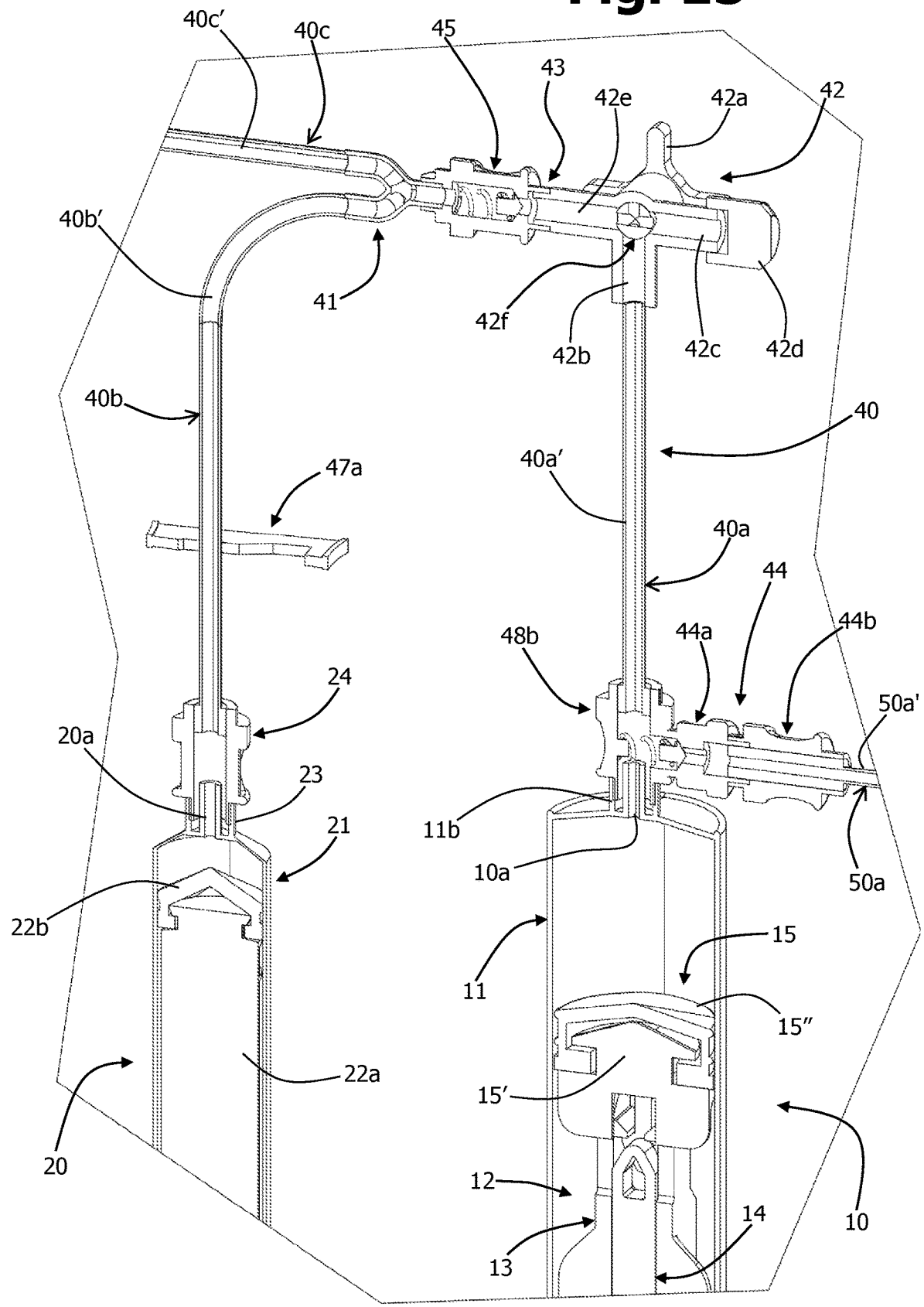
FIG. 15 is a schematic cross section, at an enlarged scale, of a portion of a medical device according to the invention.
Figure 16:
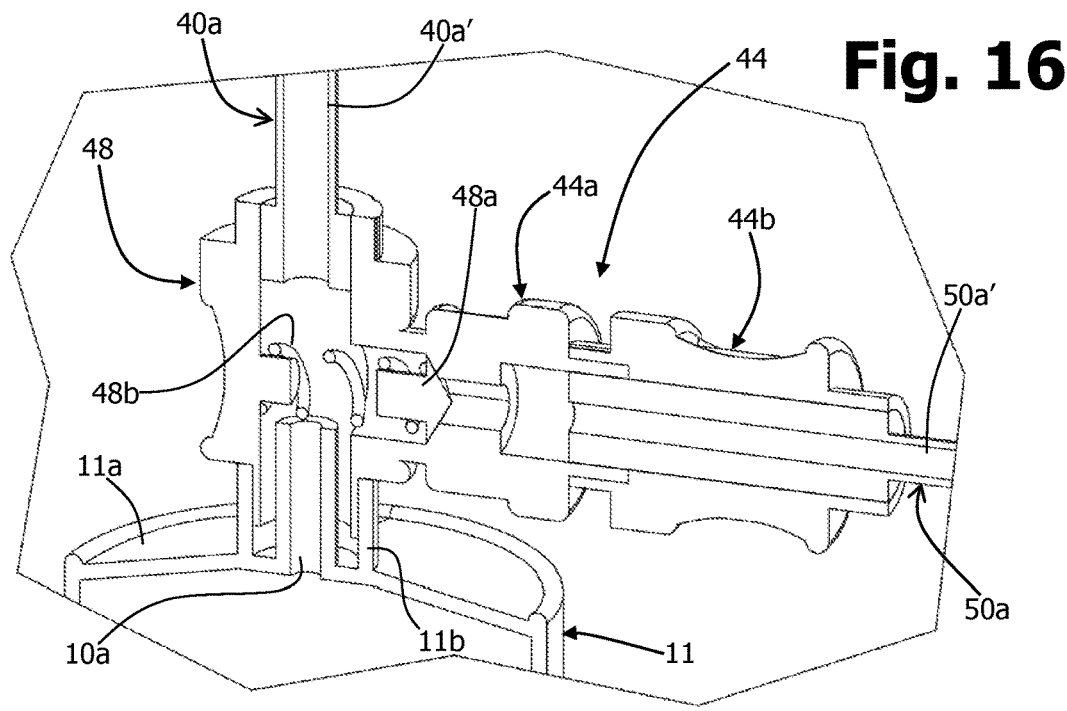
FIGS. 16 and 17 are details of FIG. 15.
Figure 17:
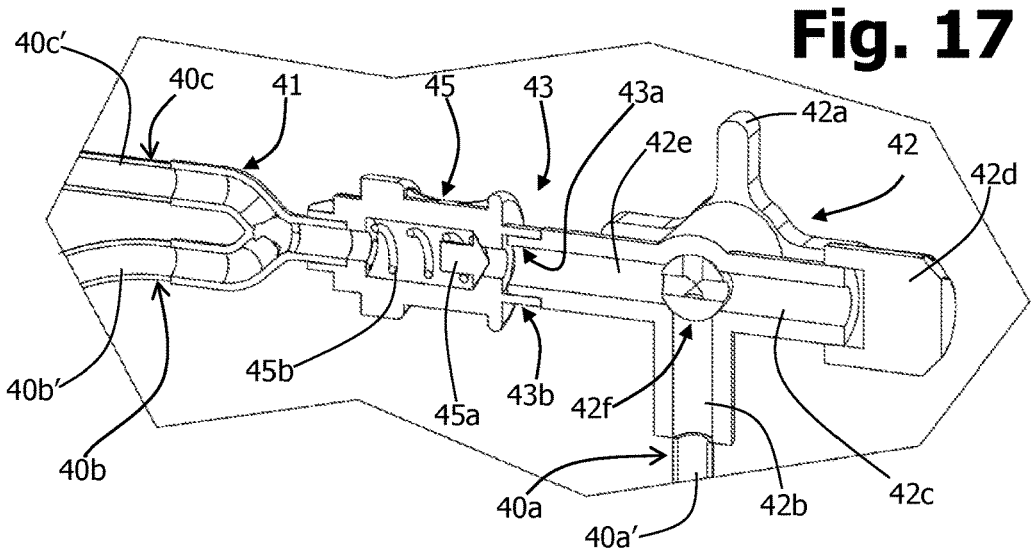

Visible in FIG. 15 is a portion of the device 1 of FIG. 1, at an enlarged scale and sectioned, whereas visible in FIGS. 16 and 17 are enlarged details of FIG. 15. From these figures, and in particular from FIG. 16, there may be noted a possible embodiment of the attachment 48, set between the tube 40a' and the attachment 11b of the container 10, where the lateral way or branching way of this attachment obtains the part 44a of the hydraulic connector 44. As has been mentioned previously, in a preferred embodiment, the attachment 48 or the connector 44 integrates or has associated a self-operating valve, aimed at preventing any possible reflux from the tube 40a' to the tube 50a' and/or any contamination from outside upon detachment of the connector part 44b.

In the example represented, present within the body of the attachment 48 (or of the connector 44) is an open/close element 48a, which is elastically forced into closing of the way internal to the part 44a, for example via a spring 48b or other elastic element. In the presence of a flow with suitable pressure coming from the tube 50a', the open/close element 48a can recede by overcoming the elastic reaction of the spring 48b. Instead, in the absence of a flow from the tube 50a', the spring 48b keeps the open/close element 48a in a position for closing the way internal to the part 44a of the connector 44. Preferentially, the force of the spring 48b and the mass of the open/close element 44a are predefined in such a way as to keep the open/close element 48a in a closing position also during the centrifuging steps (in other words, hence, the force of the spring is such as to overcome the force exerted by the mass of the open/close element in the centrifuging step). Preferably, the open/close system 48a-48b is shaped in such a way that, in the presence of a flow from the port 10a of the container 10 towards the tube 40a', the pressure of the fluid contributes to maintaining the system itself in its closing position, illustrated in FIGS. 15 and 16.

From FIG. 17 it may be appreciated how, in the embodiment illustrated, the embodiment of the self-operating valve 45 is basically similar to that of the valve 48a-48b just described above, the teachings of which may thus be considered as referring also to the valve 45. In this case, the spring 45b of the valve 45 tends to keep the corresponding open/close element 45a in a position for closing the line branch 40a, upstream of the bifurcation 41, whereas in the presence of a flow with suitable pressure from the branch 40a towards the bifurcation, the open/close element 45a can recede countering the action of the spring 45b. Preferably, also in this case, the force of the spring 45b and the mass of the open/close element 45a are predefined in such a way as to keep the open/close element 48a in a closing position also during the centrifuging steps. Also in this case, the open/close element 45a is preferentially shaped in such a way that, in the presence of a possible flow in the opposite direction (from the line branch 40c and/or 40b towards the line branch 40a), the pressure of the fluid contributes to keeping the open/close element itself in its closing position, illustrated in FIG. 17.

The structure illustrated for the valve 45 and/or 48a-48b, here substantially a one-way valve or a non-return valve, is to be understood merely as an example, given that such valves may have any structure suitable for the purpose, for example with an open/close system constituted by an elastically deformable membrane designed to open and close a port of passage or provided at the centre with a port of passage designed to open elastically when the membrane is forced by a flow or a pressure in one direction and to close elastically when the flow or pressure ceases, or else close when the membrane is forced by a flow or a pressure from an opposite direction. Such a membrane is preferably made of elastomer and/or its elasticity is such as to obtain functions similar to those of the spring 44b, 45b described previously.

Once again visible in FIG. 17 is the tap 42, within which an open/close element 42f operates, which can be turned by means of the control element 42a. In the example, as has been said, the tap 42 is a three-way tap, with the open/close element 42f that defines a tee channel. In a first angular position of the open/close element 42f (FIG. 17), the passage of fluid between the ways 42b and 42e is prevented, whereas in a second angular position of the open/close element (illustrated in FIG. 18) this passage is allowed. It should be noted, on the other hand, that also with the open/close element 42f turned through 90° in a clockwise direction with respect to FIG. 18 or in a counterclockwise direction with respect to FIG. 17, passage of fluid is allowed between the ways 42b and 42e. As has already been mentioned, the tap 42—which itself forms a part of the connection line 40—can also be replaced by a valve or tap with just two ways, of an open/close type.

In a possible variant embodiment, the line 50 of the module C, and specifically its connector part 44b, can be coupled in a different position on the line 40, once again upstream of the open/close means 42f of the tap 42, and in particular of the way 42c of the tap, instead of the plug 42d. In this case, the valve 48a-48b integrated in the attachment 48 or in the connector 44 may possibly be associated to the tap 42 or be omitted and its functions be performed by the tap 42. In such a case, with the open/close element 42f turned through 90° in a counterclockwise direction with respect to FIG. 18, the ways 42b and 42c will be in fluid communication, whereas the way 42e will be occluded, thus enabling passage of the blood and/or of the anti-coagulant into the container 10. Instead, with the open/close element 42f turned through 90° in a clockwise direction with respect to FIG. 18, it will be the ways 42b and 42e that are in fluid communication, whereas the way 42c will be occluded in order to enable flow from the container 10 towards the bifurcation 41. To an angular position of the open/close element 42f corresponding to that of FIG. 17 there will correspond, instead, closing of the way 42b, with the ways 42c and 42e in communication with one another. Such a position may be selected, for example, when the container 10 is to be handled, after the blood and/or the anti-coagulant have been loaded therein and the module C has been removed from the device.

A possible methodology of use of a device described for the purposes of separation of platelet-rich plasma from whole blood and concentration thereof is described hereinafter. It is to be assumed, for this purpose, that the device 1 is supplied already assembled, or else is assembled in the condition represented in FIG. 1 at the moment of use, preferably in sterile environment.

The clamp 47b provided on the branch 50b of the line 50 is operative (in the condition for closing the tube 50b') and, preferentially, the tap 42 is in the position of FIG. 17, i.e., a position that occludes the line 40 downstream of the attachment 48; the clamp 47c provided on the branch 50c of the line 50 is, instead, inoperative (in the condition of opening of the tube 50c'). The plunger 12 of the container 10 is made to recede, as in an ordinary syringe, for sampling from an external container or flask, via the needle 56, a certain amount of anti-coagulant, for example 5 ml which can be preferentially detected via a graduated scale present on the barrel 11 of the container 10. The clamp 47c is then brought into its operative condition, and the clamp 47b is brought into its inoperative condition. Via the needle 55 blood samples are taken from a subject, such as a person or animal, getting the plunger 12 of the container 10 to recede further.

As a variant, a sample can be taken from a container containing blood or fluid previously taken from a subject, possibly already added with anti-coagulant. In this case, the module C of the device 1 may not comprise the needle 56 and the corresponding line 50c and the connector 49, with a single line 50 instead of the lines 50a and 50b. When a certain amount of blood, for example 50 ml that can be detected via the aforesaid graduated scale, has been allowed to enter the container 10, retraction of the plunger 12 of the container 10 is stopped, and the clamp 47b is preferably brought into its operative condition. The order of the operations for sampling the anti-coagulant and the blood may possibly be reversed.

At this point, by releasing the hydraulic connector 44, the module C can be removed from the device 1, for example to enable disposal thereof, with the valve 48a-48b that closes and isolates the line 40 automatically.

The stem 13 of the corresponding plunger 12 is removed from the container 10, for example with the modalities exemplified previously. The module A, preferably connected with the module B, is put in a centrifuge in order to cause a first separation between parts of the whole-blood/anti-coagulant mixture contained in the container 10, in particular to obtain a sedimentation in at least two layers, one comprising plasma with platelets and the other comprising red and white blood cells, as a result of their different density or different weight. In this way, in the variable-volume chamber of the container 10 there will be present a layer of sediment comprising red and white blood cells and a supernatant layer comprising plasma and platelets, with a volume approximately in relationship to the haematocrit of the patient. The device 1 is positioned in the centrifuge in such a way that, following upon centrifuging, the layer of sediment will be closer to the head 15 of the plunger 12, whereas the supernatant layer will be comprised between the layer of sediment and the wall 11a of the barrel 11 provided with the attachment 11b. Preferentially, the separation of the plasma and of the platelets from the red and white blood cells is obtained with a centrifuging with low acceleration (indicatively 150-350 g, for example 260 g) for a time comprised between 8 and 15 min, for example 10.5 min, with an initial, acceleration, ramp of 30 s, and a final, deceleration, ramp of approximately 3 min. The module A, with the module B, if associated thereto, is taken out of the centrifuge, keeping the container 10 in a vertical position and preventing any agitation thereof.

Figure 18:
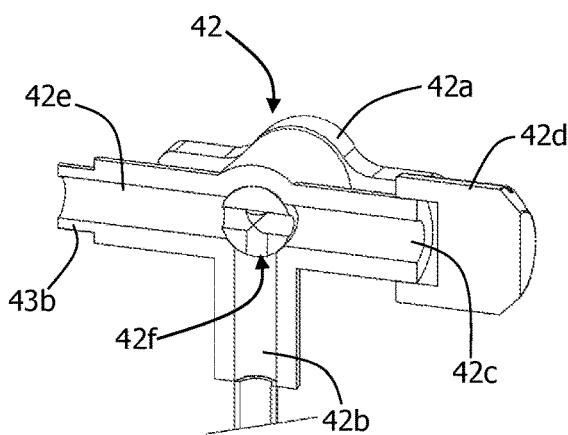
FIG. 18 is a view of a component visible in FIG. 17, in a different operative condition.

With the modules A and B connected, the tap 42 is brought into the position of FIG. 18, i.e., in a position that sets the ways 42b and 42e in communication, and the clamp 47a is brought into its operative condition, for closing the branch 40b of the line 40. It should be noted that the position illustrated in FIG. 1 for the clamp 47a is purely explanatory, since it could be in a position very close to the bifurcation 41.

By operating the plunger 12 or the plunger head 15 there is a transfer of part of the contents from the container 10 to the bag container 30 (or, as will be seen, to the container of a syringe type 20). In particular, the plunger 12 and/or its head 15 are/is made to advance so as to transfer just the supernatant layer, i.e., plasma with platelets, or a portion thereof, from the container 10 to the bag container 30. In this step, the valve 48a-48b integrated in the attachment 48 prevents exit of the plasma from the connector part 44a, while the valve 45 is opened by the thrust or pressure exerted by the blood on the open/close element 45a.

The aforesaid advance can be obtained manually or else, preferentially, with the aid of suitable automated equipment: in the former case, the container 10 must be provided once again with the corresponding plunger stem 13; in the latter case, the automated equipment—a possible embodiment of which will be described hereinafter—may be conceived so as to operate directly the head 15 of the plunger 12 of the container 10, in which case it is not necessary to re-install beforehand the corresponding stem 13. After transfer of the plasma with platelets into the bag container 30, the module A can be removed by separating the two parts of the hydraulic connector 43. Any possible exit of the plasma from the module B is prevented thanks to the presence of the valve 45, which also prevents any contamination from outside.

The module C is then put in the centrifuge, with the bag container in a substantially vertical position and with the corresponding port 30a set at the top, this positioning being enabled by the pliability of the tubes 40b', 40c'. The centrifuging carried out on the bag container 30 is more energetic than the previous one; i.e., it is a centrifuging with high acceleration, preferably in the region of 1000-1500 g for a time comprised between 6 and 15 min, for example 1200 g for 8 min. In this way, a concentration of the plasma with platelets is obtained; i.e., there is obtained, once again by sedimentation, a further separation thereof into a platelet-rich fraction and a platelet-poor fraction. In particular, a platelet-poor fraction remains uniformly suspended in the bag container 30, whereas a fraction with high concentration of platelets is found on the bottom of the bag, in a position opposite to the port 30a.

The clamp 47a is then brought into its inoperative condition for opening the tube 40b'. The plunger 22 of the container of a syringe type 20 is pulled back to draw in from the bag container 30 the platelet-poor plasma, in amounts depending upon the level of concentration that is to be obtained in the bag 30. It should be noted that, during operation of the plunger 22 of the container 20, air is not drawn in from the valve 45 in so far as the latter has a structure such as to exert a closing force greater than the negative pressure or force necessary for intake.

A possible value of platelet-poor plasma drawn in is approximately 10 ml, corresponding to 10 ml of plasma remaining in the bag together with the platelets. The total value of plasma of approximately 20 ml is obviously indicative and depends upon the patient being treated. Preferably, in any case, in the bag container 30 there remains a part of platelet-poor plasma and the platelet concentrate.

At this point, the bag container 30 can be rubbed gently in order to bring about disaggregation of the platelet concentrate previously sedimented by centrifuging. The product is then ready for being used: for this purpose, it is possible to sample the concentrate obtained, for example from the point of injection 31a of the connector 31 by means of a further syringe provided with a needle.

In a possible variant, the clamp 47a is provided on the branch 40c of the line 40, and the functions between the containers 20 and 30 are reversed. In such a case, after centrifuging carried out on the container 10 and with the clamp 47a set in the operative condition for closing the branch 40c, the plasma with platelets is transferred from the container 10 to the container of a syringe type 20, and, after removal of the module A, the module B can be put into the centrifuge. In such an embodiment, the container 20 can also have a structure similar to that of the container 10, i.e., have a plunger stem that can be separated from the corresponding plunger head. With the more energetic centrifuging carried out on the contents of the container 20 separation of the plasma is obtained into a platelet-rich fraction and a platelet-poor fraction. Positioning of the container 20 in the centrifuge will be such that the fraction richer in platelets will be closer to the head 22a of the corresponding plunger 22 and the platelet-poor fraction will be located between the enriched layer and the end of the container 20 having the port 20a.

After removal of the module B from the centrifuge, the clamp 47a is brought into its inoperative condition. The plunger 22 of the container 20 is then operated for expelling from the container itself at least part of the platelet-poor fraction, which flows into the bag container 30. In this way, within the container 20 there remains prevalently the platelet-rich fraction, for subsequent use or further treatment according to the specific protocol followed. The container 20 with platelet-rich plasma may also be separated from the rest of the module B for purposes of convenient use.

Also in this case, operation of the plunger 22 of the container of a syringe type 20 can be carried out manually or using automated equipment: in the latter case, as has been said, the container 20 may have a structure such as to enable separation between the stem and the head of the corresponding plunger.

In the previous examples, there has been hypothesized a prevalently manual use of the device 1 but, as has been mentioned, one or more steps could be carried out with the aid of automated equipment, for example by automatically controlling forward operation of the plunger head 15 of the container 10 and/or operation of the tap 42 and/or detection of the variation between the supernatant layer, comprising plasma and platelets, and the sediment layer, comprising red and white blood cells.

In its more general terms, a medical system or apparatus according to the invention, preferably automated and/or for use in combination with a medical device, preferably a device for separating a fluid, such as a device 1 of the type described previously, comprises one or more from among the following:

means for controlling an automated displacement of at least one between a plunger stem and a plunger head of a container of the medical device;

means for controlling an automated displacement of a control element of a valve means of the medical device;

detection means for detecting a characteristic of a flow present within a fluidic connection line of the medical device;

electromagnetic or optical sensor means, preferably comprising at least one emitter and at least one receiver of electromagnetic radiation;

supporting means for a container of the medical device, preferably configured for keeping said container in a generally vertical position;

a member for actuation of one from among a plunger stem, a plunger head, and a container of the medical device and means for controlling displacement of the actuation member;

sensor means for detecting the position of an actuation member with respect to a plunger head of a container of the medical device;

a stationary support for an electromagnetic or optical sensor system, the support preferably including, substantially in a position corresponding to the optical sensor system, a positioning seat for a stretch of a connection line of the medical device;

a support for a valve means of the medical device;
an electromagnetic or optical sensor system including two electromagnetic or optical sensors in sequence or in series with respect to one another;
a support associated to which is an element provided with means shaped for positioning a stretch of a connection line of the medical device in a position corresponding to a sensor system of the apparatus, in particular within a corresponding seat;
a system for actuating a valve means of the medical device, preferably comprising a movable member shaped for coupling to a control element of the aforesaid valve means; and
means for reading and/or for unidirectional or bidirectional communication of data with an identification element of the medical device.

Figure 19:
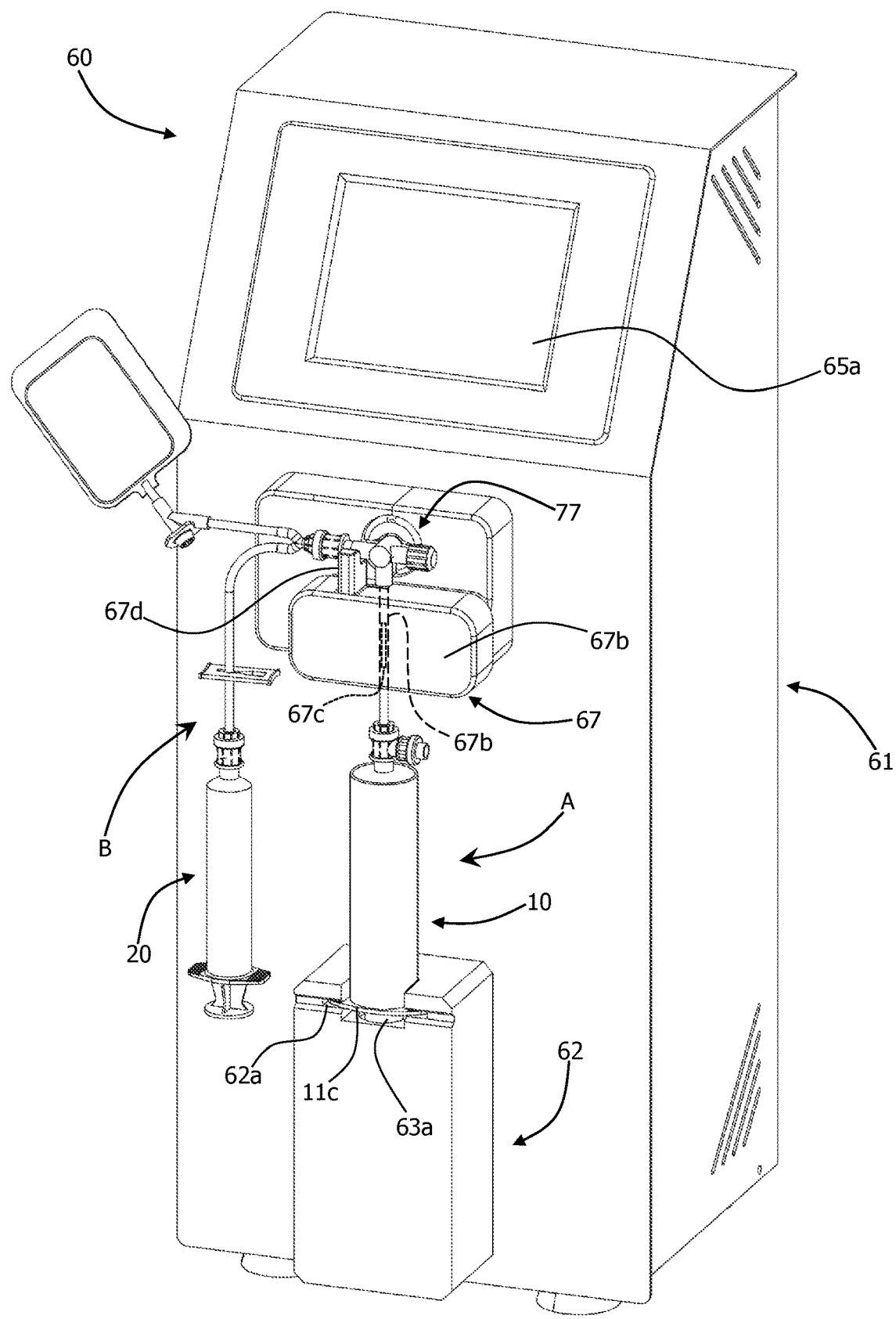
FIG. 19 is a schematic perspective view of an apparatus that can be used in combination with a device according to the invention including at least the modules of FIGS. 2 and 3.
Figure 20:
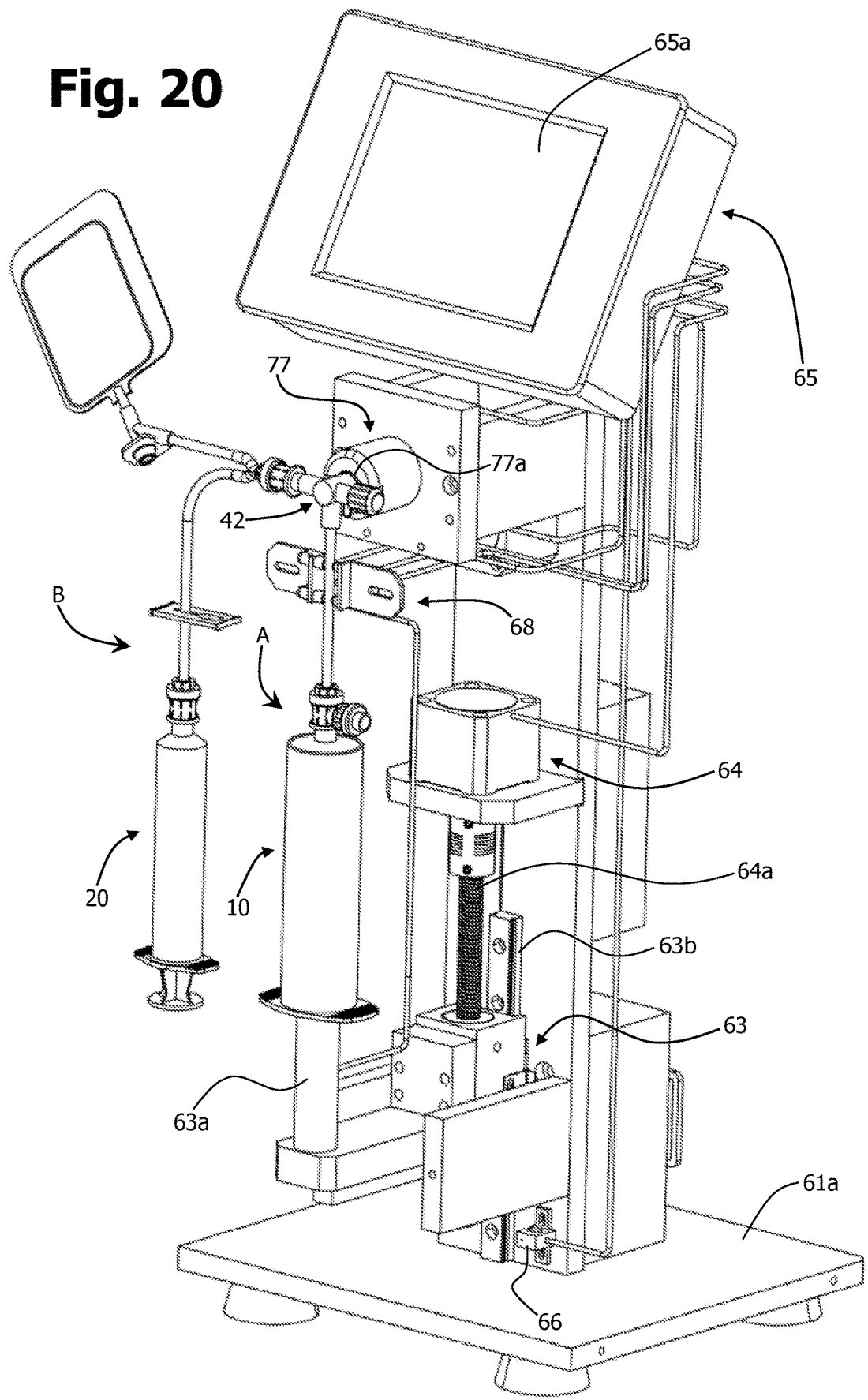
FIG. 20 is a schematic perspective view of the apparatus of FIG. 19, with a corresponding casing removed.
Figure 21:
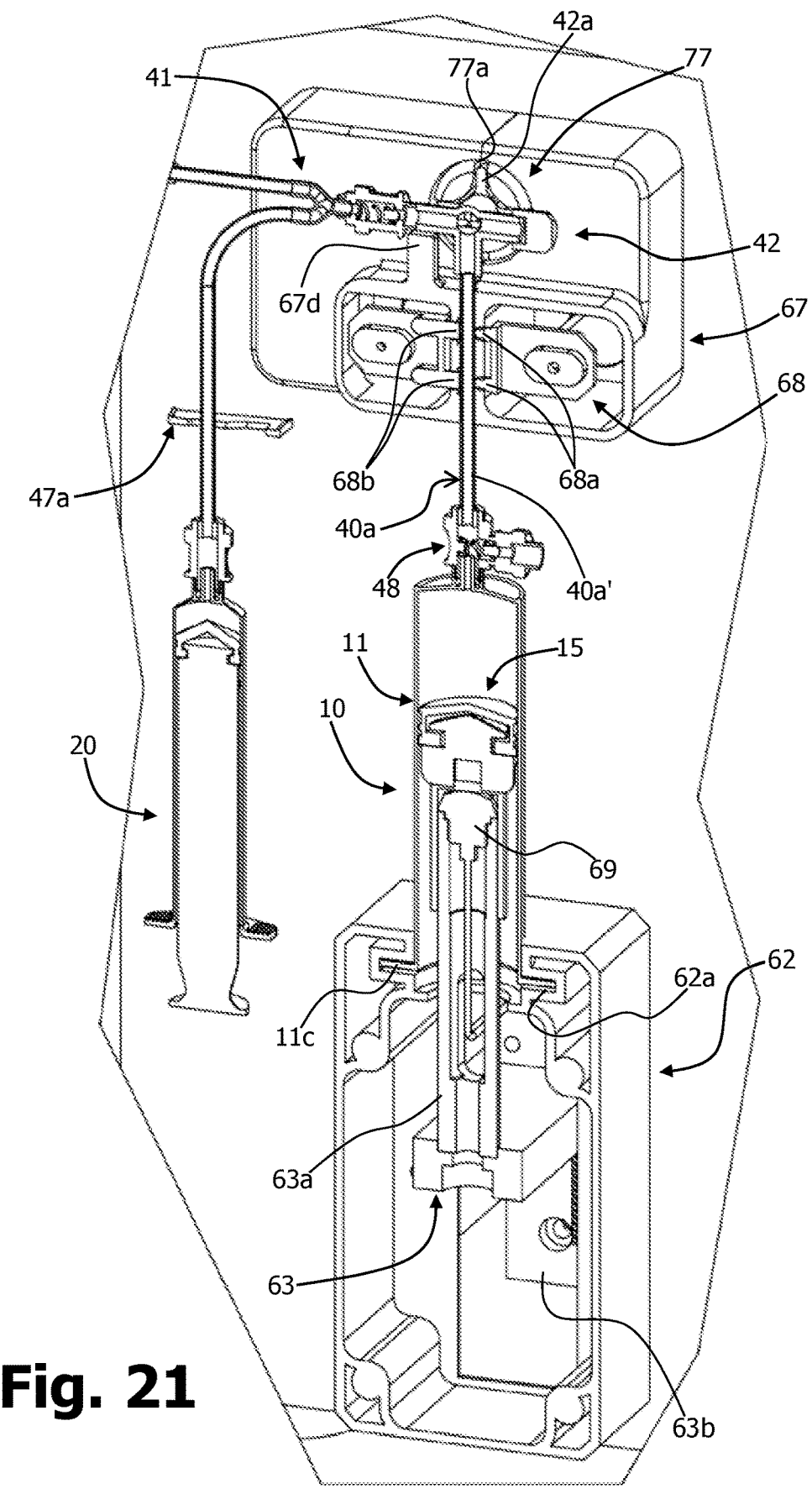
FIG. 21 is a sectioned view of a portion of the apparatus of FIG. 19.

A possible embodiment of an automated equipment is represented schematically by way of example in FIGS. 19-21, where it is designated as a whole by 60, and in which the modules A and B of the device 1 described previously are highlighted.

The apparatus 60 has a load-bearing structure or body 61, preferably provided with a stationary support 62 for housing and/or positioning the container 10. In the example, the aforesaid support 62 is located at the front and configured for setting the container 10 in a vertical position, i.e., with the port 10a and attachment 11b upwards. In the example, the support includes a slot or seat 62a for receiving the flange 11c (FIG. 5) of the barrel 11 of the container 10, from which the corresponding stem 13 has previously been removed. Movable within a hollow part of the support 62 is an actuation member 63a designed to move the plunger head 15 of the container 10 in a controlled way. As may be seen in FIG. 20, the actuation member 63a belongs to a structure 63 that is vertically movable in opposite directions with respect to a base 61a and is driven via an actuator 64. The actuator 64 may for example be an electric motor with screw-operated shaft 64a, associated to which—for example via an auger—is the structure 63, so that the latter can be displaced vertically in a guided way. In the example, the structure has a part configured substantially like a slide, coupled to a corresponding vertical guide 63b.

The position of the structure 63, and hence of the actuation member 63a, may be controlled via suitable sensors forming part of the control system of the apparatus, designated as a whole by 65. One of the sensors referred to above, for example a proximity sensor or a microswitch, is designated by 66.

The control system 65, the program or software of which monitors general operation of the apparatus 60, includes suitable control means, for example a programmable logic circuit (PLC), and user-interface means, for example a display 65a of a touch-screen type, for setting the commands and required operating parameters.

Preferentially, the apparatus 60 also includes a support 67 (FIG. 19) for an electromagnetic or optical sensor system, preferably a sensor of transparency or opacity, and/or shutoff or deviation valves or means.

The above sensor system, designated by 68 in FIGS. 20 and 21, includes at least one emitter and at least one receiver of electromagnetic radiation, for example light radiation. Provided in one embodiment is an emitter of a signal with a predefined wavelength and a receiver designed to detect the aforesaid signal and/or its variations. Preferentially, the sensor system is conceived for transmitting the electromagnetic or light signal through a stretch of a line or tube of the device 1 that is transparent to the aforesaid signal, where the latter varies at the receiver end (for example, it is attenuated or in any case altered) as a function of the composition of the flow passing through the tube. For instance, passage of a greater amount or concentration of given substances or particles in the fluid (such as red and/or white blood cells) in the stretch of tube set between the transmitter and the receiver prevents or attenuates passage of the signal between the transmitter and the receiver, with the aforesaid variation of signal that is thus indicative of the composition of the flow passing through.

Alternatively, the sensor system 68 is conceived for transmitting an electromagnetic or light signal that at least in part undergoes deviation or refraction owing to the presence of substances or particles in the fluid. As in the previous case, passage of a different composition or greater amount or concentration of given substances or particles in the fluid in the aforesaid stretch of tube causes a different refraction of the signal that can be detected at the receiver end, indicating, for example, transition between plasma and red or white blood cells.

The sensor system may also be prearranged for detecting the colouring of the flow passing through the tube, for example on the basis of detection of the absorption of light by substances or particles present in the fluid.

The support 67 is shaped so as to define a passage or seat 67a (represented dashed in FIG. 19 in so far as it is covered by a removable lid 67b), where there can be inserted a stretch of the tube 40a' (or, if need be, of the tube 40b', in the case where the container of a syringe type 20 is replaced by a container similar to the container 10 and it is intended to automate the final step of the separation method, preferably according to the variant described previously).

In a position corresponding to the aforesaid seat 67a, preferably mounted on sides set at an angle with respect to one another or opposite to one another, are the aforesaid emitter (for example, a light-emitting diode or LED) and receiver (for example, a photoresistance or a phototransistor). Preferably, two optical sensors are provided in sequence or in series with respect to one another, such as a pair of emitters in sequence and a pair of corresponding receivers in sequence, designated by 68a and 68b in FIG. 21. Preferentially, the lid 67b is shaped in such a way as to push and/or position a corresponding stretch of the tube 40a' or 40b' in a correct position within the seat 67a, in a position corresponding to the sensor system 60. For this purpose, the side of the lid facing the seat for the lid 67b is preferably provided with an appropriately shaped internal relief, designated as a whole by 67c in FIG. 19.

The distance between the emitters, on one side, and the receivers, on the other, i.e., the distance between two optical sensors in sequence, may for example be approximately 10 mm.

Preferentially, the support 67 integrating the optical sensor system is shaped also for defining means for supporting or positioning the tap 42, designated as a whole by 67d in FIGS. 19 and 21, or else a support independent of the support 67 may be provided for this purpose. Preferentially, the supporting means 67d are configured for coupling at least in part with the shape of the body of the tap 42, and/or parts of the device 1 close to the tap, in particular in order to support it and/or keep it in position during operations performed on the tap itself, such as movement of its control element 42a.

With reference once again to FIG. 21, operative within the actuation member 63a, and in particular in a position corresponding to its upper end, is a sensor 69, for example a microswitch, used by the system 65 for controlling the position of the member 63. In particular, the sensor 69 has the function of detecting the mechanical contact between the top of the member 63*a* and the plunger head 15 of the container 10 when the member 63*a* is raised via the corresponding actuation system.

In an advantageous embodiment, a further actuation system is also provided, controlled by the control system 65 of the apparatus 60, for controlling, in an automated way, switching of the tap 42 between at least some of the positions described previously.

For this purpose, the control element 42*a* of the tap 42 can be shaped for coupling to a corresponding actuation member, preferably provided with a seat having a shape at least in part complementary to that of the control element. A further actuation system of this sort is exemplified in FIG. 21, where designated by 77 is a rotatable member, to which there can be coupled the control element 42*a* of the tap 42, which is operated via an actuator (not represented), such as an angularly movable actuator or an electric motor with rotatable shaft. The rotatable member 77 preferentially has a seat or impression 77*a* designed to receive the control element 42*a* at least partially, i.e., at least to the extent where it is possible to impose a rotation thereon. In the example, this seat 77*a* is set low down and is in part complementary to the control member 42*a* of the tap 42, which is preferably provided with radial lobes and/or is shaped so as to be operable both manually and in an automated way.

Other shapes useful for the purpose for obtaining rotation of the control element 42*a* via the rotatable member 77 are evidently possible. The control element 42*a* and the seat 77*a* could have other mutually complementary or coupleable shapes, for example of a polygonal type (triangular, square, pentagonal, etc.) or star-shaped type, or complex shapes comprising linear stretches and/or curved stretches.

Preferentially, at the start of an operating cycle of the apparatus, the member 77 has an angular position such that the control element 42*a* of the tap can be coupled in the seat 77*a* only when the tap itself is in a predefined position, for example the position of FIG. 18, or in any case a position such that the open/close element 42*f* sets the ways 42*b* and 42*e* in communication (it is not on the other hand excluded that the aforesaid predefined position corresponds to the condition for closing the passages between the ways 42*b* and 42*e*, as for example in FIG. 17).

According to an operative example, after the container 10 has been coupled to the support 62, and after—via the user interface 65*a*—the parameters possibly requested have been entered and a command for start of cycle has been imparted, the actuator 64 moves the structure 63 from below upwards, for example starting from a lowered end-of-travel position (not represented). In the case where the predefined position of the tap were the closing position, for example as in FIG. 17, the system 65 previously issues a command for rotation of the member 77 in order to bring the tap itself into the opening position, for example that of FIG. 18. At a certain point of rising of the structure 63, the control system 65 detects, via the sensor 69, contact between the member 63*a* and the plunger head 15, in this way acquiring information regarding the position of the head itself. Detection of this position may, for example, be useful for enabling first a relatively fast advance of the member 63*a* and then a slower movement thereof, following upon contact between the head 15 and the member 63*a*. The sensor 69 hence enables detection of the position of effective start of travel or thrust on the plunger head 15, and thus automatic detection of the effective travel or distance of movement of the head itself.

After contact, the member 63*a* then starts to bring about displacement of the head 15, which itself may be controlled at different speeds, for example with an faster initial step and a slower final step (such as an initial speed of displacement of the head 15 of 2 mm/s for a distance of 8 mm and then a speed of 0.05 mm/s up to conclusion of the cycle). During movement of the plunger head 15, the flow within the line branch 40*a* is intercepted by the optical system 68, in particular so as to measure the transmittance or other optical characteristic of the fluid that is passing, preferably in two points of the tube 40*a*' set at a distance from one another (in a way corresponding to the distance between two sensors 68, such as the distance existing between the emitters 68*a* and the receivers 68*b* of each pair). Preferentially, the control electronics carries out automatic calibration with respect to the value detected by the optical system upon turning-on of the apparatus 60, before and/or after positioning of the device 1 on the apparatus. When the plasma starts to rise as a result of the thrust exerted by the member 63*a* on the plunger head 15, the optical system 68 detects a first variation of the optical characteristic considered (for example, the transmittance), corresponding to the air-plasma transition in the branch 40*a*, and a second variation of the same optical characteristic when the red and/or white blood cells pass, i.e., upon passage of plasma-blood cells in the branch 40*a*. The control system 65 then interrupts operation of the motor 64, and hence of the member 63*a*, when both of the receivers 68*b* of the system have detected the presence of red and/or white blood cells. Sampling of the signal may for example be carried out at a frequency of approximately 1 kHz, which corresponds to a displacement of the fluid of approximately 50 µm between one sampling and the next.

Furthermore, when the control system 65 detects, via the optical sensor 68, the aforesaid second variation of the optical characteristic considered, indicating the start of flow of the reject part (containing the red and white blood cells), also the actuator associated to the member 77 is operated so as to turn the control element 42*a* of the tap 42 to bring its open/close element into the position of FIG. 17 or in any case into a position such as to prevent any flow between the ways 42*b* and 42*e*.

The system is programmed so as to convey into the bag container 30 the plasma and the platelets and leave instead the red and white blood cells in the module A, i.e., in the container 10 and in the corresponding branch of the connection way 40. For the purpose of complete recovery of all the platelet-enriched plasma there may be predefined an appropriate delay or further travel, between the moment of optical detection and the moment of interruption of the movement of the actuation member 63*a* and actuation of the member 77. For instance, with a container 10, having an average diameter of 29.2 mm, after optical detection, the plunger rises once again by 0.57 mm, corresponding to a distance traversed in the tube 40*a*' (internal diameter of 2.8 mm) of 62.1 mm, recovering a volume of plasma of 381.9 mm$^3$.

In one embodiment, the medical device forming the subject of the invention comprises at least one filtering member, preferably for ultrafiltration, for example on at least one branch of the first connection line 40. Filtration is preferably of a tangential type and based upon the use of filtering elements that will enable the corpuscular part of the plasma (i.e., the platelets and growth factors that may be present in the plasma) to be withheld in the line 40 and will separate part of the liquid fraction thereof, principally constituted by water. Preferentially, an aforesaid filtering member—that may include one or more porous membranes—belongs to the module B.

Figure 22:
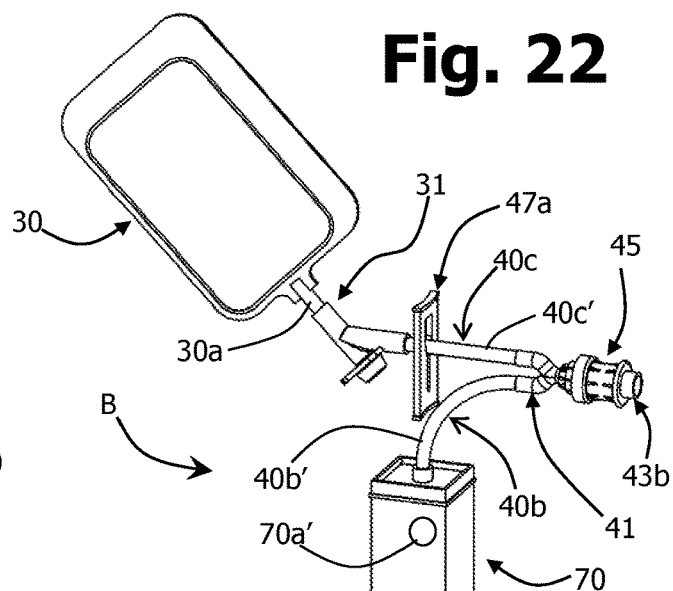
FIG. 22 is a schematic perspective view of a module of a medical device according to a variant embodiment of the invention.

An embodiment in this sense is exemplified in FIG. 22, where designated as a whole by 70 is a filtering member operatively set on the branch 40b of the connection line 40. As will be seen, a filtering member can be set on the branch 40c or, possibly, each branch 40b, 40c can be provided with a respective filtering member.

Figure 23:
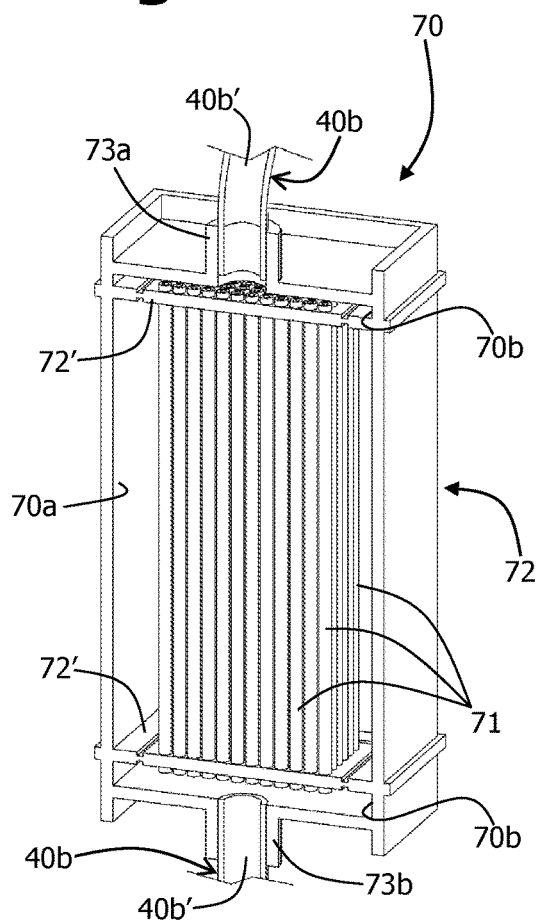
FIGS. 23 and 24 are a sectioned view of a filtering member of the module of FIG. 22, at an enlarged scale, and a corresponding detail, respectively.

Illustrated in cross-sectional view in FIG. 23 is the member 70, prearranged for carrying out a filtration substantially of a tangential type, via a plurality of hollow porous fibres, some of which are designated by 71, substantially shaped like small tubes with porous cylindrical walls. The active part of the member 70 may include between 30 and 100 hollow fibres, preferably 40-60 fibres, with a length comprised between 40 and 80 mm, preferably 50 mm. The internal diameter of the hollow fibres is indicatively comprised between 100 and 500 μm, preferably 250 μm. The hollow fibres preferably have porosity with a size comprised between 5 and 15 kdalton, very preferably 7 kdalton, or comprised between 1 and 5 nm, so as to withhold the platelets but also possible growth factors present in the plasma.

Figure 24:
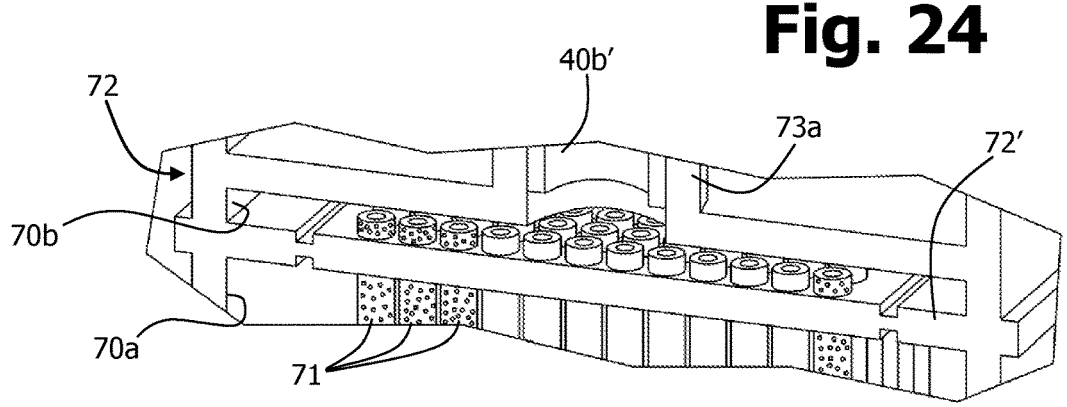

The member 70 includes a casing body 72, in the cavity of which two transverse walls 72' define a central collection chamber 70a and two terminal connection chambers 70b, each facing an axial end wall of the body 72 that is provided with a respective duct or attachment 73a, 73b for connection along the line branch 40b. The fibres 71 have respective through portions in the walls 72' in order to keep the fibres themselves in position substantially like a bundle. In this way, the open ends of the fibres 71 are located within the connection chambers 70b provided with the ducts 73, 73b, as may be clearly seen in FIG. 24, where the pores of some fibres are highlighted. The intermediate and prevalent part of the fibres 71 extends instead within the collection chamber 70a substantially in an axial direction. As may be inferred, via the ducts 73a, 73b, the filtering member 70 is connected in series between two stretches of the line 40b, whilst the fibres 71 connect the terminal chambers 70b in parallel to one another. The chamber 70a is designed to collect a discarded liquid fraction of the plasma, in particular represented by water containing molecules below the size of porosity of the fibres 71. Preferentially, the chamber 70a has at least one passage 70a' (FIG. 22) provided with a valve or an appropriate membrane (of a GoreTex® type) that is permeable to air but not to liquids in order to enable the air to exit when the aforesaid discarded liquid fraction enters the chamber 70a.

The module B of FIG. 22, which may have characteristics in common to the module B described previously, can be coupled, for example, to the module A in order to obtain a device according to the invention, in particular so as to include valve means designed to enable or prevent a flow of fluid through the branches 40a, 40b and 40c of the connection line 40. These valve means may comprise, for example, the tap 42 (here not represented), and the clamp 47a, which is here on the branch 40c, and the self-operating valve 45.

In general, the aforesaid valve means may assume a first operative condition, in which a flow of fluid along the line 40 between the container 10 and the container 30 (or the container 20, as has been explained) is allowed, and a second operative condition, in which a flow of fluid along the line 40 between the container 30 and the container 20, or vice versa, is allowed.

The use of a filtering member enables, if so required, omission of the second step of plasma centrifuging envisaged by the methodologies described previously. In particular, after the plasma with platelets has been transferred from the container 10 to the container 30, for example with the modalities already described previously, it is possible to get the plasma itself to pass one or more times through the filtering member 70 by operating the plunger 22 of the container of a syringe type 20, also in opposite directions, with the valve means represented by the clamp 47a in the respective condition that enables passage of the plasma between the containers 30 and 20. For instance, in the case where repeated passages through the member 70 are to be carried out, the plunger 22 can be operated in one direction to draw in the plasma with platelets from the container 30 to the container 20, and then be operated in the opposite direction, in order to force the residue of plasma with platelets from the container 20 to the container 30, and so forth (alternatively, as has been explained, the plasma with platelets can be initially delivered to the container 20 instead of to the container 30, in which case the order of actuation of the plunger 22 will be reversed with respect to what has just been indicated).

At each passage through the filtering member 70 the plasma passes first into a chamber 70b, then through the hollow fibres 71, and then into the other chamber 70b. In the passage through the fibres 71, the plasma loses water and small molecules through the corresponding pores, with a filtration of a tangential type, preferably minimizing the contact of the platelets with the porous cylindrical wall of the fibres 71 and preventing both loss of a part thereof owing to adhesion on the internal surfaces of the fibres and their possible activation caused by mechanical stress.

For the aforesaid contact not to occur, or for it to be as limited as possible, it is preferable for the flow within the member 70 to be of a laminar type: in this way, the particles, in particular the platelets, tend to concentrate where the speed of the fluid is greater, namely along the axis of symmetry of the fibres 71.

The waste liquid that traverses the pores of the intermediate part of the fibres 71 reaches the collection chamber 70a, whilst the remaining part of the liquid fraction, in which the concentration of platelets is increased, can proceed until it reaches the container 20 (or, in the case of a further cycle, the container 30, with reverse operation of the plunger 22). In this way, it is possible obtain the desired concentration of platelet-enriched plasma. These cycles of concentration or movement of the plunger 22, which may be carried out manually or automatically via an apparatus, can terminate with the residue of platelet-rich plasma in the bag container 30, which enables a more convenient storage at a low temperature and a transport in conditions of sterility, or else in the container of a syringe type 20, which enables a more immediate use.

The porous membranes or hollow fibres used in the application proposed can be obtained with purposely designed materials, for example polyvinylidene fluoride (PVDF), polyether sulphone (PES), polypropylene (PP), polyethylene (PE), polysulphone (PS), polyacrylonitrile (PAN), polyvinyl chloride (PVC), polyamide (PA), polyarylether sulphone (PAES), polyvinyl pyrrolidone (PVP), or mixtures thereof.

A different embodiment is exemplified in FIG. 25, where the filtering member, here designated by 70', is operatively set on the branch 40c of the connection line 40. As for the previous case, on the other hand, the member 70' may be set on the branch 40b or, possibly, each branch 40b, 40c may be provided with a respective filtering member. It is also possible to provide one member 70 on a branch and one member 70' on the other branch.

FIG. 26 is a cross-sectional view of the member 70', which in this case is prearranged for carrying out a filtration substantially of a tangential type via a plane porous membrane, designated by 71'. The member 70' includes a casing body 72, preferably made up of at least two parts 72a and 72b that can be coupled together in a fluid-tight way, with the filtering membrane 71' set in between.

The part 72a is provided with corresponding ducts 73a, 73b for connection along the branch 40c, which are preferably angled ducts, for example L-shaped ducts, so as to have a corresponding proximal end facing the membrane 71'. The part 72b defines the collection chamber 70a for collecting the discarded liquid fraction of the plasma, which extends underneath the membrane 71. Also in this case, the member 70' has at least one passage 70a' provided with an appropriate valve or membrane for enabling the waste fraction to reach the collection chamber 70a.

Irrespective of the specific embodiment of the casing body 72, it is preferably shaped so as to define a gap, which extends substantially parallel to the membrane 71', on the side opposite to the collection chamber 70a. The gap extends between the proximal ends of the ducts 73a, 73b and the membrane itself, preferably obtaining a chamber with an extensive surface but with a reduced height, in particular in order for the membrane to be lapped better by the fluid. A possible embodiment of such a gap is designated by 74 in FIG. 27, where some pores of the membrane 71', designated by 71a, are also highlighted.

Operation of a device according to the invention integrating the module B of FIGS. 25-27 is similar to what has been described above with reference to FIGS. 22-24. Also in this case, with the clamp 47a in the condition of opening (here on the branch 40b) it is possible to get the plasma to pass one or more times through the filtering member 70' by operating the plunger 22 of the container of a syringe type 20. At each passage through the filtering member 70', the plasma passes through the gap 74, lapping the membrane 71' with a preferably laminar flow. Part of its liquid fraction penetrates into the pores 71a of the membrane 71' to reach the collection chamber 70a, whereas the remaining part of the liquid fraction, where the concentration of platelets is increased, can proceed until it reaches the container 20 (or, in the case of a further cycle, the container 30, with reverse operation of the plunger 22), as for the embodiment of FIGS. 22-24, in order to obtain the desired concentration of platelet-enriched plasma.

Also for the application referred to in FIGS. 25-27 purposely designed membranes can be used, preferably made of a material of the type referred to previously and/or with filtering characteristics similar to the hollow fibres already referred to or with a porosity designed to withhold preferably molecules above 7 kdalton, for example, membranes for nanofiltration and reverse osmosis of the type generally used for haemoconcentration processes.

A filtering member, in particular with anti-bacterial functions, can also be provided along the connection line of one of the sampling devices 55, 56, in particular the device 56, also in addition to one or more filters provided on the line 40. For instance, as illustrated in FIGS. 28 and 29, an anti-bacterial filter 80 may be set between the device 56 and the connector 49, or more in general downstream of the device 56. In such an embodiment, operative within the body of the filter 80 are one or more membranes 81 with pores sized so as to allow flow of the liquid—here the anti-coagulant—and withhold, instead, possible bacteria.

FIGS. 28 and 29 highlight clamp valves 47b' and 47c' on the branches 50b and 50c of the line 50, which have a structure different from the ones previously designated by 47b and 47c, but perform similar functions. Similar clamps can be used on the modules A and/or B also in the previous embodiments.

In one embodiment, such as the one exemplified in FIG. 28, on the branch 40a there may be present a further clamp 47, in particular located in the proximity of the attachment 48, for enabling closing of the branch 40a towards the tap 42 during sampling of a fluid (blood and/or anti-coagulant) via the module C and/or during centrifuging of the module A. Use of such a clamp 47 has the purpose of preventing undesirable passage of the fluid along the branch 40a. After sampling of the fluid or centrifuging, the clamp 47 is brought into a position for opening the branch 40a. A similar clamp can be provided also in the embodiments described previously.

From the foregoing description, the characteristics of the present invention emerge clearly, as likewise do its advantages, which are principally represented by the simplicity of embodiment of the disposable medical device proposed, by its contained cost, by its precision and simplicity of use and handling, and by its safety.

The modular construction of the device is advantageous also in relation to the possibility of combining together modules having different characteristics, according to the requirements of use. For instance, it is possible to envisage modules or stages C differentiated from one another as regards type or size of the needle so that they adapt better to the characteristics of the patient (adult or child), or once again modules or stages A and B differentiated on the basis of the subject and/or the type of fluid to be treated or separated, for example with a different bag or a container of a syringe type, or with different volumes, or with the possible addition of other devices.

The modularity referred to is particularly useful in the steps of production of the device, enabling manufacture and warehousing of the various separate modules, which can be assembled on the basis of the specific requirements of the clientele. The modularity of the device 1 avoids the need to stock devices 1 in multiple complete configurations; i.e., it enables warehousing of the various separate modules, to be assembled rapidly if need be, with a reduction of the costs of storage and a faster production and/or delivery to the customer. The modules A and/or B and/or C can be produced separately, assembled together to produce a device 1, sterilized and packaged for subsequent use.

Also the methodologies of separation and concentration proposed, as well as the corresponding equipment, prove advantageous as regards their simplicity of implementation, effectiveness, and precision.

Particularly advantageous is the possibility of separating the modules of the device, without any risk of contamination of the fluid by the external environment, in particular considering the fact that the shutoff-valve means or means for automatic closing of the ducts are preferably set in the proximity of the hydraulic connectors or inside them. The possibility of separation between the modules moreover enables a more convenient handling of the device during its steps of use.

It is clear for the person skilled in the art that numerous variations may be made to the devices and to the methods described by way of example herein, without thereby departing from the scope of the invention as defined by the annexed claims.

A filter having a structure similar to that of the filter 80, provided, however, with a membrane 81 designed withhold the leukocytes, could be provided on at least one of the branches 40b, 40c of the module B, preferably in series to the filter 70, 70' described previously, when such a filter 70, 70' is envisaged.

Among the possible variants, the possibility may here be mentioned of providing a separation device including substantially just two containers, which can preferably be connected together via a line provided with a filtering member of the type designated previously by 70 or 70', for example the containers 10 and 30, or else 10 and 20, or once again the containers 20 and 30, at least one of which is possibly of a centrifugable type, in order to carry out a separation of a fluid into at least two fractions, in particular according to the methodology described previously.

The self-operating valve or valves used in the device do not necessarily have to be integrated in respective attachments or connectors, but can be operatively arranged in the proximity of the aforesaid connectors, on a corresponding line branch or tube.

The modules A and/or B and/or C or their parts can be combined together in a way and/or in a number different from what has been illustrated and described herein, for providing variants of the device according to the invention.

According to a preferential variant of the invention (not represented), the device 1 envisages at least one identification element, for example an identification element containing data. Such an element may, for example, be a barcode or else an electronic identification device, preferably of a wireless type (for example, a radiofrequency or RFID device), designed to transmit and/or receive data. In such an embodiment, the apparatus 60 is preferably provided with means for detecting and/or transmitting data to the aforesaid identification element (for example, an optical sensor or a radiofrequency receiving and/or transmitting device).

Preferentially, the identification element is integrated or associated to at least one part or a module of the device 1, preferably associated to a container thereof, such as for example a bag container (30) or a container of a syringe type (10, 20). For instance, an element of an RFID type can be integrated or mounted in the barrel or in the plunger of a container of a syringe type, in particular in a protected area thereof and/or an area not subject to contact with the fluid.

In the case of an identification element of an electronic type, this is preferably provided with memory means, for example for storing information regarding at least one from among the type of the device 1, the fluid sampled, and the data that can be detected by the control system 65 of the apparatus 60. Information of this type can be used, for example, for the purposes of automatic setting of operations or controls made by the apparatus (for example, for certifying the correct combination of the device 1 to the apparatus 60 and/or for controlling operation of the apparatus 60 on the basis of the fluid contained in the device 1 and/or for automatic configuration of at least part of the operations and/or detections that can be made by the apparatus 60). The identification element may also be designed to store data regarding at least one subject involved in the treatment of the fluid (for example, the subject from whom the blood sample has been taken and/or the subject who is to receive the platelet-enriched plasma).

In a possible variant (not represented), the apparatus 60 is prearranged so as to enable operation of the plunger stem of the container 10, instead of just its head 15. In such an embodiment, then, after centrifuging has been carried out on the container 10, the latter must once again be provided with the corresponding stem 13, which is thus coupled to the corresponding head 15. In this case, the actuation member, previously designated by 63a, of the apparatus 60 is replaced by a different element, designed to couple the stem 13 in its outer part to the barrel 11. For this purpose, for example, the stem 13 can be provided with a transverse seat or cavity (designated by 13b only in FIGS. 5-7), preferably a through seat. The seat 13b is located in particular in a proximal end region of the plunger stem, preferably in such a way that at least one part of the seat itself is located in a portion of the stem 13 that is once again on the outside of the barrel 11.

In such a variant, the apparatus 60 may be prearranged for carrying out also retraction of the plunger 12 of the container 10, for example for the purposes of automated sampling of the anti-coagulant or of the blood and/or for intake or sampling of parts or fractions of the blood.

For this purpose, the actuation member can be prearranged for coupling to a proximal end of the plunger 12, for example configured as a substantially fork-shaped transverse member, with an upper part thereof designed to penetrate into the seat 13b and a lower part thereof that is, instead, underneath the proximal end of the plunger 13. A may be inferred, with such a conformation, the actuation member, when translated upwards or downwards, brings about advance or retraction of the stem 13, respectively, and hence of the plunger head 15. With an embodiment of this sort, when the container 20 has a structure similar to that of the container 10 or has in any case a plunger designed to couple to a corresponding actuation member of the apparatus 60, it is possible to automate, using the apparatus, also the methodology of filtering with repeated passages described previously with reference to FIGS. 22-24 and 25-27. It should be noted, on the other hand, that implementation of this methodology using the apparatus 60 does not necessarily presuppose that the containers 10 and 20 have the same structure. What counts, in fact, is that the actuation member of the apparatus 60 is configured for coupling to the plunger of the container 20 so as to be able to cause both advance and retraction thereof.

It is also possible to configure the apparatus 60 in such a way as to keep the plunger or the plunger head of the container of a syringe type 10 and/or 20 in a stationary position, moving, instead, the corresponding barrel 11 and/or 21 in an axial direction (for example, rendering the part of the support 63 of FIG. 19 that integrates the seat 62a) displaceable.

As explained previously, the devices and/or systems and/or equipment and/or the methods according to the invention find preferred application for separation and concentration of platelet-rich plasma from whole blood, but it will be appreciated that they can be used also in other medical branches, preferably in all those medical branches in which it is useful to carry out separation and/or concentration and/or control of liquids and/or fractions of biological liquids, tissues in the fluid state, or liquid medical substances.

The invention claimed is:

1. A medical device for separating at least a blood fraction from whole blood by centrifugation, comprising:
    a first container for receiving whole blood to be separated into blood fractions, a second container for receiving a first blood fraction of the whole blood, and a third container for receiving a second blood fraction of the whole blood, the containers each having a first port for fluid inlet and/or fluid outlet;

a first connection line having a first line branch, with a first end that can be associated to the first port of the first container, and at least one intermediate bifurcation for defining at least one second line branch and one third line branch defining respective second ends of the first connection line, the second ends of the first connection line being associatable to the first port of the second container and to the first port of the third container, respectively;

valve means on the first connection line, the valve means operable for enabling or preventing a fluidic flow through at least one from among the first line branch, the second line branch, and the third line branch, the valve means including an operable valve set on the first line branch in an intermediate position between said first end and said intermediate bifurcation, wherein the first container comprises:
a hollow container body having an elongated shape with a first end and a second end, the hollow container body having the respective first port at the first end and a second port at the second end;
a plunger, which is associated in a movable way to the hollow container body and has a plunger head that is slidably engaged in a fluid-tight way inside the hollow container body, for defining thereby a fluid-collection chamber that is in communication with the first port, the plunger having a plunger stem that can be displaced through the second port of the hollow container body for varying the position of the plunger head and thereby varying the volume of the fluid-collection chamber, the plunger stem being associated in a releasable way to the plunger head, wherein the device has a modular structure comprising a plurality of modules, connected together in a separable way, for enabling separation thereof according to the operating step of use of the device, and including at least one first centrifugable module, which comprises at least the first container and a corresponding portion of the first connection line, and a second centrifugable module, which comprises at least one of the second or third containers with a corresponding portion of the first connection line, and wherein provided at the interface between two modules of the modular structure are releasable connectors, comprising at least two mutually coupling connector parts, each connector part belonging to a corresponding module.

2. The medical device according to claim 1, wherein the modular structure includes a third module that comprises at least one fluid-sampling device selected between a device for sampling the whole blood to be separated, or a device for sampling an anti-coagulant.

3. The medical device according to claim 1, further comprising at least one second connection line for setting the first connection line in fluid communication with a device for sampling the whole blood to be separated or a device for sampling an anti-coagulant.

4. The medical device according to claim 3, comprising the device for sampling the whole blood and the device for sampling the anticoagulant, wherein the second connection line includes an outlet branch, for connection to the first branch of the first connection line, and two inlet branches each associated to a respective one of said sampling devices and converging into the outlet branch.

5. The medical device according to claim 1, moreover comprising at least one self-operating valve operatively associated to one said releasable connector, the at least one self-operating valve being configured for preventing at least one of the following:
any contamination from outside of the whole blood or blood fractions thereof following upon separation between two modules; and
any reflux between two different branches of a connection line or between two connection lines.

6. The medical device according to claim 5, wherein the operable valve and the self-operating valve belong to two different modules of said plurality of modules.

7. The medical device according to claim 5,
wherein the modular structure includes a third module that comprises at least one fluid-sampling device selected between a device for sampling the whole blood to be separated or a device for sampling an anticoagulant, and
the self-operating valve being designed for preventing any contamination from outside following upon separation between the first module and the third module and/or for preventing any reflux from the first connection line to a second connection line belonging to the third module, and being operatively set at an interface area between the first branch of the first connection line and an outlet branch of the second connection line.

8. The medical device according to claim 5, wherein the self-operating valve comprises an open/close element elastically forced in a closed position thereof, to prevent a fluid flow from occurring in a first flow direction through the associated releasable connector, the open/close element being moved to an open position thereof by a fluid flow occurring through the associated releasable connector in second flow direction which is opposite to the first flow direction.

9. The medical device according to claim 8, wherein the self-operating valve comprises a spring for urging the open/close element in the first flow direction.

10. The medical device according to claim 8, wherein the self-operating valve is integrated in the associated releasable connector.

11. The medical device according to claim 1, wherein the operable valve comprise a shutoff valve designed to be controlled manually and/or mechanically.

12. The medical device according to claim 11,
comprising a self-operating valve for preventing any contamination from outside following upon separation between the first module and the second module and/or for preventing any reflux from the second branch and/or from the third branch of the first connection line into the corresponding first branch,
wherein the self-operating valve is set on the first branch of the first connection line between the intermediate bifurcation and the shutoff valve.

13. The medical device according to claim 1, wherein the second module comprises the second container and the third container, the second container being a compressible container and the third container having a movable plunger.

14. The medical device according to claim 1, comprising at least one filtering member on at least one said line branch.

15. The medical device according to claim 1, wherein one or more modules of the modular structure further comprise at least one respective shutoff member on a branch of a corresponding connection line.

16. A system for separating whole blood into blood fractions by centrifugation, comprising a medical device according to claim 1 and an automated apparatus which includes at least one from among:
- means for controlling an automated displacement of at least one of the plunger stem or the plunger head of the first container of the medical device;
- means for controlling an automated displacement of a control element of the operable valve of the medical device;
- detection means for detecting a characteristic of a flow present within a fluidic connection line of the medical device;
- electromagnetic or optical sensor means, comprising at least one emitter and at least one receiver of electromagnetic radiation;
- supporting means for keeping at least one of said containers of the medical device in a generally vertical position;
- an actuation member for actuating the plunger stem or the plunger head of the first container of the medical device, and means for controlling displacement of the actuation member;
- sensor means for detecting a position of an actuation member of the automated apparatus with respect to the plunger head of the first container of the medical device;
- a stationary support for an electromagnetic or optical sensor system, the stationary support including a positioning seat for a portion of a connection line of the medical device;
- a support for the operable valve of the medical device;
- an electromagnetic or optical sensor system including two electromagnetic or optical sensors in sequence or in series with respect to one another;
- a support associated to which is an element provided with means shaped for setting a portion of a fluidic connection line of the medical device in a position corresponding to a sensor system of the automated apparatus;
- a system for actuating the operable valve of the medical device, comprising a movable member shaped for coupling to a control element of said operable valve; or
- means for reading data and/or for unidirectional or bidirectional communication of data with an identification element of the medical device.

17. A method for separating whole blood into blood fractions by centrifugation, comprising the steps of:
   i) providing a medical device according to claim 1;
   ii) sampling, via the first container, the whole blood to be separated, and possibly an anti-coagulant, by moving at least the plunger head of the first container in a direction of extraction thereof with respect to the hollow container body;
   iii) subjecting to centrifuging the contents of the first container, in order to separate or stratify said contents into a layer of sediment closer to the plunger head, including red and white blood cells, and a supernatant layer closer to the first port of the first container, including plasma and platelets;
   iv) transferring at least part of the supernatant layer from the first container to the second container by actuating at least the plunger head of the first container in a direction of insertion thereof with respect to the hollow container body;
   v) subjecting to centrifuging the contents of the second container, for separating it into a platelet-rich fraction and a platelet-poor fraction; and
   vi) transferring at least part of the platelet-poor fraction from the second container to the third container, in such a way that the platelet-rich fraction remains prevalently in the second container.

18. The medical device according to claim 1, wherein one of said fractions includes at least one of plasma and platelets.

19. A medical device for separating at least one first blood fraction from whole blood by centrifugation, comprising:
a first container for receiving whole blood to be separated into blood fractions, a second container for receiving a first blood fraction of the whole blood, and a third container for receiving a second blood fraction of the whole blood, the containers each having a first port for fluid inlet and/or fluid outlet;
a first connection line having a first line branch, with a first end that can be associated to the first port of the first container, and at least one intermediate bifurcation for defining at least one second line branch and one third line branch defining respective second ends of the first connection line, the second ends of the first connection line being associatable to the first port of the second container and to the first port of the third container, respectively;
the medical device moreover comprising a valve on the first connection line, operable for enabling or preventing a fluidic flow through at least one from among the first line branch, the second line branch, and the third line branch, the valve being an operable valve set on the first line branch in an intermediate position between said first end and said intermediate bifurcation,
wherein the first container comprises:
   a hollow container body having an elongated shape with a first end and a second end, the hollow container body having the respective first port at the first end and a second port at the second end;
   a plunger, which is associated in a movable way to the hollow container body and has a plunger head that is slidably engaged in a fluid-tight way inside the hollow container body, for defining thereby a fluid-collection chamber that is in communication with the first port, the plunger having a plunger stem that can be displaced through the second port of the hollow container body for varying the position of the plunger head and thereby varying the volume of the fluid-collection chamber, the plunger stem being associated in a releasable way to the plunger head,
wherein the device has a modular structure comprising a plurality of modules, connected together in a separable way, for enabling separation thereof according to the operating step of use of the device, and including at least one first centrifugable module, which comprises at least the first container and a corresponding portion of the first connection line, and a second centrifugable module, which comprises at least one of the second or third containers with a corresponding portion of the first connection line,
wherein provided at the interface between two modules of the modular structure are releasable connectors, comprising at least two mutually coupling connector parts, each connector part belonging to a corresponding module,
the medical device moreover comprising at least one self-operating valve operatively associated to one said releasable connector, the self-operating valve comprising an open/close element elastically forced in a closed position thereof, to prevent a fluid flow from occurring in a first flow direction through the associated releasable connector, the open/close element being moved to an open position thereof by a fluid flow occurring through the associated releasable connector in second flow direction which is opposite to the first flow direction.

* * * * *

UNITED STATES PATENT AND TRADEMARK OFFICE
CERTIFICATE OF CORRECTION

PATENT NO. : 10,549,025 B2
APPLICATION NO. : 15/036640
DATED : February 4, 2020
INVENTOR(S) : Zanin et al.

Page 1 of 1

It is certified that error appears in the above-identified patent and that said Letters Patent is hereby corrected as shown below:

On the Title Page

In the Assignee Item (73): Delete "ELETEK S.P.A." and insert -- ELTEK S.P.A. --

Signed and Sealed this
Thirty-first Day of March, 2020

Andrei Iancu
*Director of the United States Patent and Trademark Office*